US009260478B2

(12) United States Patent
Hu et al.

(10) Patent No.: US 9,260,478 B2
(45) Date of Patent: Feb. 16, 2016

(54) POTENT AND EFFICIENT CYTOTOXIC PEPTIDES AND ANTIBODY-DRUG CONJUGATES THEREOF AND THEIR SYNTHESIS

(71) Applicants: Shanghui Hu, Cranbury, NJ (US); Lucy Xiumin Zhao, San Diego, CA (US); Jinying Ning, Beijing (CN); Xufang Tian, Cranbury, NJ (US)

(72) Inventors: Shanghui Hu, Cranbury, NJ (US); Lucy Xiumin Zhao, San Diego, CA (US); Jinying Ning, Beijing (CN); Xufang Tian, Cranbury, NJ (US)

( * ) Notice: Subject to any disclaimer, the term of this patent is extended or adjusted under 35 U.S.C. 154(b) by 0 days.

(21) Appl. No.: 14/515,807

(22) Filed: Oct. 16, 2014

(65) Prior Publication Data

US 2015/0284425 A1    Oct. 8, 2015

Related U.S. Application Data

(60) Provisional application No. 61/975,046, filed on Apr. 4, 2014.

(51) Int. Cl.
*A61K 47/48*    (2006.01)
*C07K 16/30*    (2006.01)
*A61P 35/00*    (2006.01)
*C07K 5/02*    (2006.01)
*C07K 7/02*    (2006.01)
*A61K 38/00*    (2006.01)

(52) U.S. Cl.
CPC ......... *C07K 5/0207* (2013.01); *A61K 47/48438* (2013.01); *C07K 7/02* (2013.01); *A61K 38/00* (2013.01)

(58) Field of Classification Search
None
See application file for complete search history.

(56) References Cited

U.S. PATENT DOCUMENTS

| 7,659,241 B2 | 2/2010 | Senter et al. |
| 2005/0009751 A1 | 1/2005 | Senter et al. |
| 2005/0238649 A1 | 10/2005 | Doronina et al. |
| 2013/0129753 A1 | 5/2013 | Doroski et al. |

FOREIGN PATENT DOCUMENTS

| WO | 02088172 | 11/2002 |
| WO | 2004010957 | 2/2004 |
| WO | 2004073656 | 9/2004 |
| WO | 2012143495 | 10/2012 |

*Primary Examiner* — Thomas S Heard
(74) *Attorney, Agent, or Firm* — VLP Law Group LLP; Kent H. Cheng

(57) ABSTRACT

The present invention provides a family of novel cytotoxic pentapeptides, which show potent antitumor activities against several cancer lines. The antibody-drug conjugates prepared from those pentapeptides can efficiently kill cancer cells.

3 Claims, 4 Drawing Sheets

Fig. 1A. IC50 curves of payload 18, IgG1-vc18 and H-vc18 against HCC1954
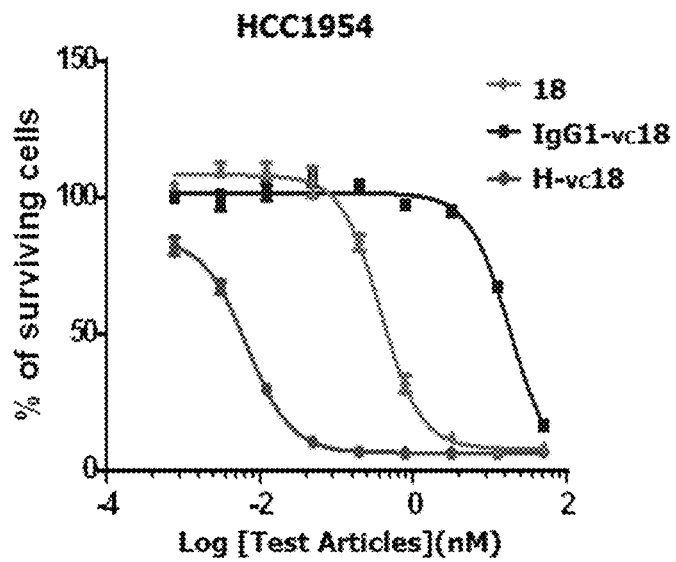
Fig. 1B. IC50 curves of payload 18, IgG1-vc18 and H-vc18 against SK-BR-3
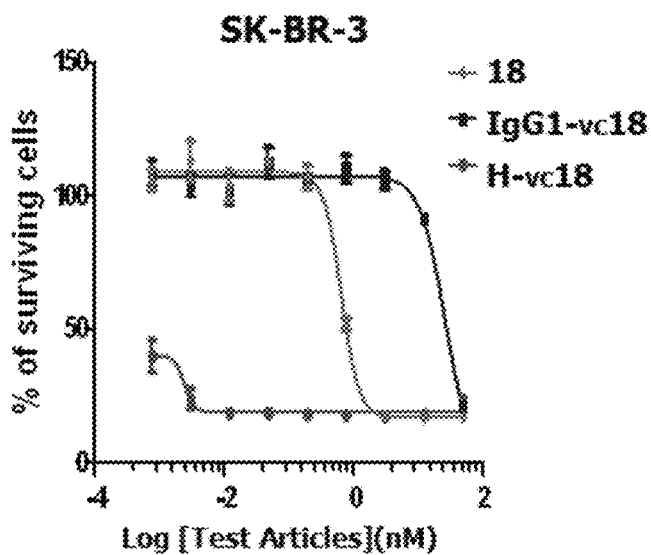

Fig. 1C. IC50 curves of payload 18, IgG1-vc18 and H-vc18 against MCF-7
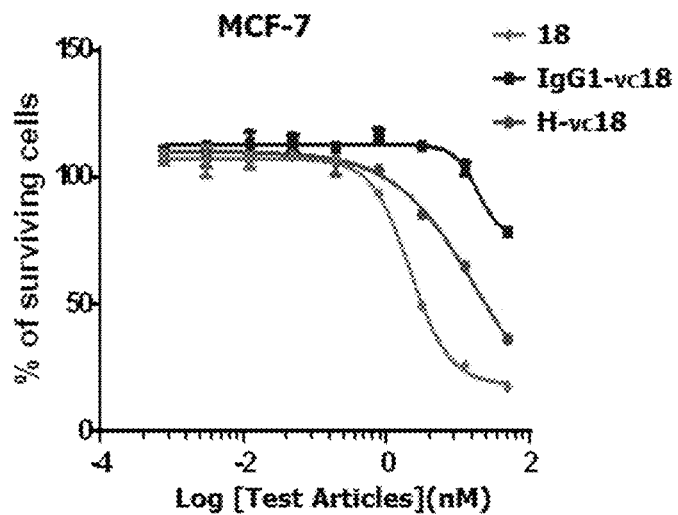
Fig. 2A. Selectivity between H-vc18 & IgG1-drug control against Her2 positive cancer cell lines HCC 1954 and SK-BR-3
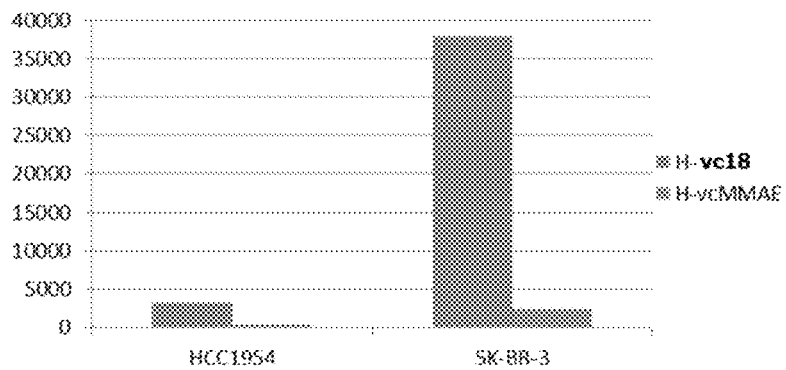

Fig 2B.Selectivity between Her2 positive cancer cell lines& MCF-7
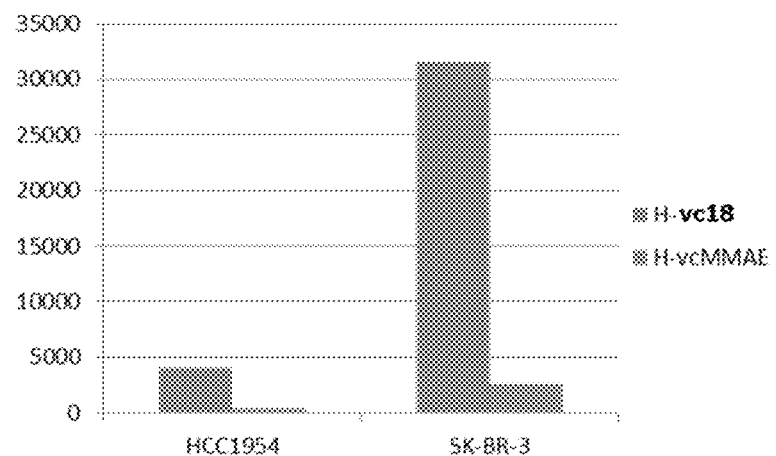

Fig 2C. Efficiency ratio between free drugs vs ADCs against Cancer cell lines HCC 1954 and SK-BR-3
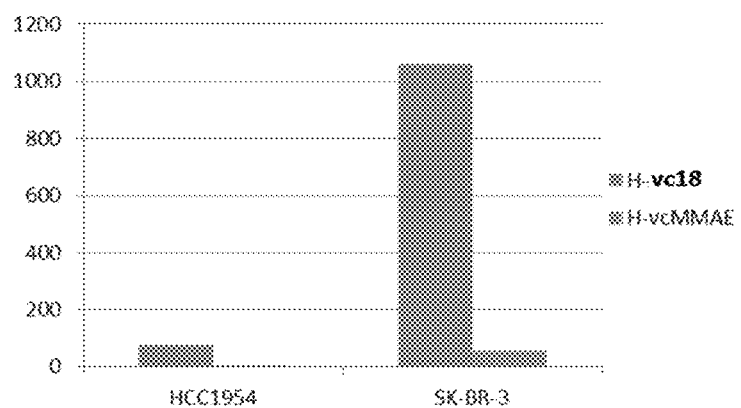

POTENT AND EFFICIENT CYTOTOXIC PEPTIDES AND ANTIBODY-DRUG CONJUGATES THEREOF AND THEIR SYNTHESIS

CROSS-REFERENCE TO RELATED APPLICATIONS

The present application claims priority to U.S. Provisional Patent Application 61/975,046, filed Apr. 4, 2014, the entire contents of which is incorporated herein by reference.

TECHNICAL FIELD

The present invention relates to the discovery and preparation of a family of novel cytotoxic pentapeptides. These compounds show potent antitumor activities against several cancer lines. The antibody-drug conjugates prepared from those pentapeptides can efficiently kill cancer cells.

BACKGROUND ART

Since the introduction of the concept of antibody-drug conjugates (ADCs) three decades ago, this area has been advanced greatly along with improved ADC and linker technology. The approved drugs Adcetris (Brentuximabvedotin) in 2011 and Kadcyla (Trastuzumabemtansine) in 2013 have dramatically increased the interests and efforts on ADC drug discovery and development all over pharmaceutical, biopharmaceutical and research institutions worldwide. Success ratios of ADC drugs in clinical trials are largely dependent on ADC biomolecules's efficacy and toxicity, especially when the free drugs could not be cleaved and released from the whole ADC molecules in biological system before reaching the targeted cancer cells. So far there are only three main families of cytotoxins successfully used for ADC drugs developed in clinical trials. Among them, auristatin, such as monomethylauristatin E (MMAE) derived from natural dolastatin 10 has been used for Adcetris, an approved drug for the treatment of Hodgkin lymphoma/ALCL non-Hodgkin lymphoma. MMAE is generally conjugated antibodies through a peptide-cleavable self-immolating linkage system. [Gail Lewis Phillips, Antibody-Drug conjugates and Immunotoxins, Humana Press, 2013]. Maytansinoids have been used for marketing Kadcyla for treatment of late stage Her2 positive breast. Auristatins and maytansinoids are microtubule-binding agents. The third one is calicheamicin, a DNA-damaging agent, which was also used for several ADCs developed in clinical trials. Some of the problems facing the first generation of ADCs are in employing ADCs bearing more highly potent agents. The use of ADCs bearing more highly potent effectors will increase the probability of delivering a therapeutic dose to tumors cells that have low antigen expression or have poor processing. The properties of high potency, stability in circulation, reasonable aqueous solubility, and efficient metabolite release in targeted cells will be highly important in designing new payloads for ADCs.

Thus, there remains a need to discover novel cytotoxins which show higher potency against cancer cells, but lower toxicity for normal cells. Our current disclosure addresses the invention of a novel family of dolastatin pentapeptide-like cytotoxins and biological results of the ADC molecules prepared thereof.

REFERENCES

1). PCT Int. Appl., 2002088172, 7 Nov. 2002 (MMAE preparation)
2). PCT Int. Appl., 2012143495, 26 Oct. 2012.
3). US2004010957 (Drug-linker preparation)
4). US 20050238649A1 (drug-linker preparation and antibody conjugation)
5). US 20050009751 (pentapeptide preparation)
6). US20130129753 (Aib novel pentapeptide preparation)
7). Doronina S O, et al, *Nat. Biotechnology* 2003, 21, 778-84.
8). *Tetrahedron,* 63, 6155-6123 (2007).

SUMMARY OF THE INVENTION

Definitions and Abbreviations

1) Antibody

An antibody (Ab), also known as an immunoglobulin (Ig), is a large Y-shape protein produced by B cells that is used by the immune system to identify and neutralize foreign objects such as bacteria and viruses. The antibody recognizes a unique part of the foreign target, called an antigen. Each tip of the "Y" of an antibody contains aparatope (a structure analogous to a lock) that is specific for one particular epitope (similarly analogous to a key) on an antigen, allowing these two structures to bind together with precision. Using this binding mechanism, an antibody can tag a microbe or an infected cell for attack by other parts of the immune system, or can neutralize its target directly (for example, by blocking a part of a microbe that is essential for its invasion and survival). The production of antibodies is the main function of the humoral immune system.

2) Drug

A drug is a substance which may have medicinal, intoxicating, performance enhancing or other effects when taken or put into a human body or the body of another animal and is not considered a food or exclusively a food.

3) Antibody Drug Conjugate (ADC)

Antibody-drug conjugates or ADCs are a new class of highly potent biopharmaceutical drugs designed as a targeted therapy for the treatment of people with cancer. ADCs are complex molecules composed of an antibody (a whole mAb or an antibody fragment such as a single-chain variable fragment [scFv]) linked, via a stable, chemical, linker with labile bonds, to a biological active cytotoxic (anticancer) payload or drug.[8] Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional chemotherapeutic agents, antibody-drug conjugates target and attack the cancer cell so that healthy cells are less severely affected.

4) Drug Conjugate

More broadly a cytotoxic drug may be linked to a Ligand via a stable, chemical, linker. The Ligand unit (L-) includes within its scope any unit of a Ligand (L) that binds or reactively associates or complexes with a receptor, antigen or other receptive moiety associated with a given target-cell population. A Ligand can be any molecule that binds to, complexes with or reacts with a moiety of a cell population sought to be therapeutically or otherwise biologically modified. The Ligand unit acts to deliver the Drug unit to the particular target cell population with which the Ligand unit reacts. Such Ligands include, but are not limited to, large molecular weight proteins such as, for example, full-length antibodies, antibody fragments, smaller molecular weight proteins, polypeptide or peptides, and lectins. The scope of the Ligand unit (L-) is discussed in U.S. Pat. No. 7,659,241, starting at col. 101, line 34, which is incorporated herein by reference.

5) Cytotoxicity

Cytotoxicity is the quality of being toxic to cells. Examples of toxic agents are an immune cell or some types of venom (e.g. from the puff adder or brown recluse spider).

6). Microtubules

Microtubules are a component of the cytoskeleton, found throughout the cytoplasm. These tubular polymers of tubulin can grow as long as 50 micrometers, with an average length of 25 μm, and are highly dynamic. The outer diameter of a microtubule is about 24 nm while the inner diameter is about 12 nm. They are found in eukaryotic cells and are formed by the polymerization of a dimer of two globular proteins, alpha and beta tubulin.

7). Tubulin Inhibitors

Tubulin inhibitors interfere directly with the tubulin system which is in contrast to those drugs acting on DNA for cancer chemotherapy. Microtubules play an important role in eukaryotic cells. Alpha- and beta-tubulin, the main components of microtubules, have gained considerable interest because of their function and biophysical properties and has become the subject of intense study. The addition of tubulin ligands can affect microtubule stability and function, including mitosis, cell motion and intracellular organelle transport. Tubulin binding molecules have generated significant interest after the introduction of the taxanes into clinical oncology and the general use of the *vinca* alkaloids. These compounds inhibit cell mitosis by binding to the protein tubulin in the mitotic spindle and preventing polymerization or depolymerization into the microtubules. This mode of action is also shared with another natural agent called colchicine.

8). Cancer

Cancer known medically as a malign antneoplasm, is a broad group of diseases involving unregulated cell growth. In cancer, cells divide and grow uncontrollably, forming malignant tumors, and invading nearby parts of the body. The cancer may also spread to more distant parts of the body through the lymphatic system or bloodstream. Not all tumors are cancerous; benign tumors do not invade neighboring tissues and do not spread throughout the body. There are over 200 different known cancers that affect humans.

9). Antibody Activity

Preventing or inhibiting the formation or growth of tumors

Abbreviations n-BuLi; n-Butyllithium
Cbz: Carboxybenzyl
DAD: Diode array detection
DEA: Diethanolamine
DEPC: Diethyl phosphoryl cyanide
DIPA: N,N-Diisopropylethylamine
DIPEA: N,N-Diisopropylethylamine
DMA: N,N-Dimethylacetamide
DMSO: Dimethylsufoxide
DTNB: 5,5'-Dithio-bis-(2-nitrobenzoic acid)
DTT: Dithiothreitol
HPLC: High performance liquid chromatography
IgG-1: Isotope-control human:
LC-MS: Liquid Chromatography mass spectrometer
MMAE: Monomethylauristatinnorephedrine
MMAF: Monomethylauristatin phenylalanine
MMAD: Monomethyldolastatin10
TFA: Trifluoroacetic acid
TLC: Thin layer Chromatography

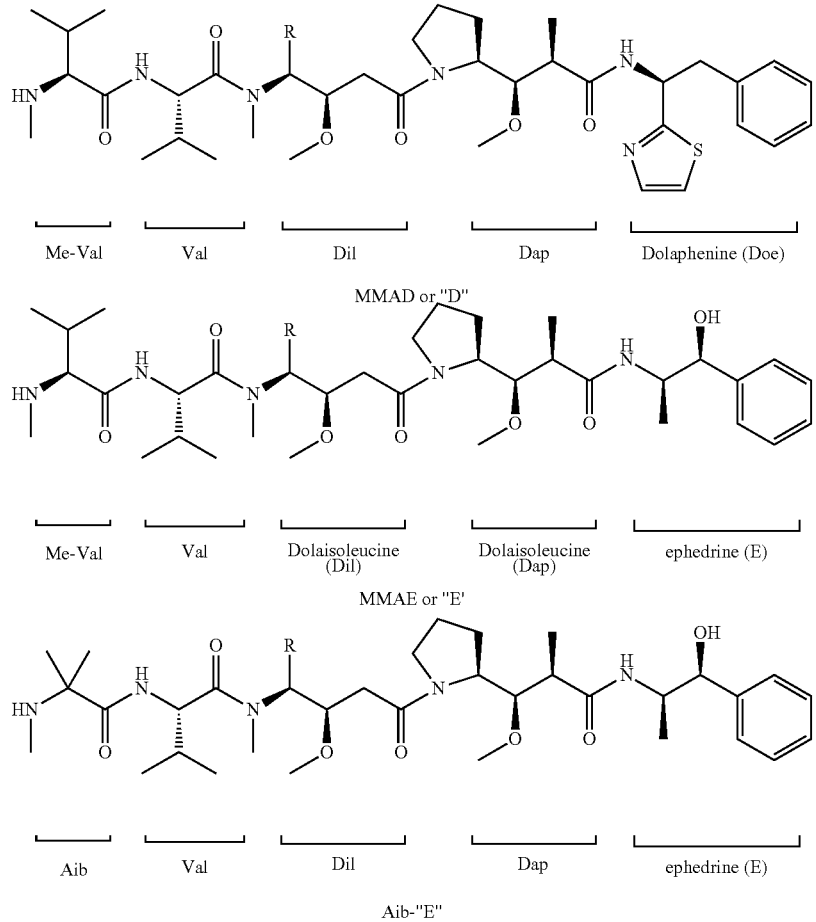

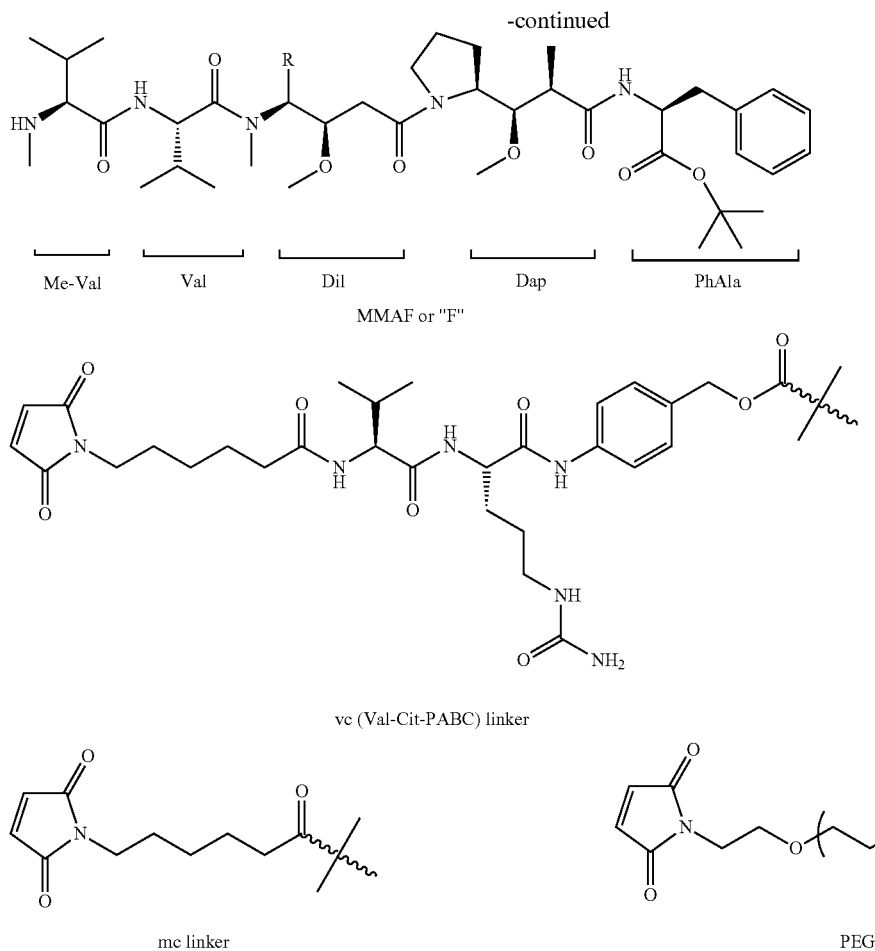

MMAF or "F"

vc (Val-Cit-PABC) linker mc linker

PEG linker

SUMMARY OF THE INVENTION

The present invention discloses a family of novel cytotoxic pentapeptides, which show potent antitumor activities against several cancer cells, including Hela, A549, MCF-7, HCC-1954 and SK-BR-3, but not limited to those cancer cell lines.

In the present disclosure, we invented a new type of cytotoxic pentapeptides derived from dolastatin 10 (MMAD), auristatins E and F (MMAE and MMAF). One core amino acid, dolaisoleucine (DiI) in MMAD, MMAE or MMAF (structures shown in Scheme) was replaced with a variety of unnatural aminoacids. For all the compounds invented in this disclosure, the novel "dil" pieces were synthesized starting from different unnatural amino acids or a molecule which could be chemically converted to amino acids by similar procedures published in WO2002088172 and US20130129753.

Compounds and Antibody Drug Conjugates

An aspect of the invention relates to compound having the structure:

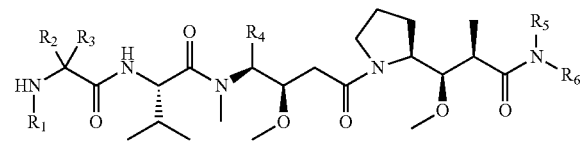

$R_1$ is H, C1-C8 alkyl;
$R_2$ is C1-C8 alkyl, C1-C8 alkyloxy, C3-C8 carbocycle, aryl, C3-C8 heterocycle, or C1-C8 haloalkyl;
$R_3$ is C1-C8 alkyl, C1-C8 alkyloxy, C3-C8 carbocycle, aryl, C3-C8 heterocycle, or C1-C8 haloalkyl;
or
$R_2$ and $R_3$ form a C3-C8 carbocycle or a C3-C8 heterocycle;
$R_4$ is H, C1-C8 alkyl, —C3-C8 carbocycle, -aryl, —C1-C8 alkyl-aryl, —C1-C8 alkyl-(C3-C8 carbocycle), —C3-C8 heterocycle and —C1-C8 alkyl-(C3-C8 heterocycle), with the proviso that $R_4$ is not sec butyl;
$R_5$ is H or C1-C8 alkyl;
$R_6$ is selected from the group consisting of:

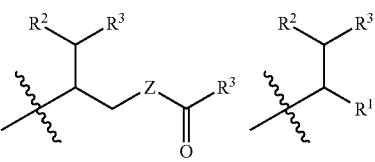

Z is —O—, —S—, —NH— or —N($R^5$)—; $R^2$ is selected from the group consisting of —H, —OH, —NH$_2$, NHR$^5$, —N(R$^5$)$_2$, —C1-C8 alkyl, —C3-C8 carbocycle, —O—(C1-C8 alkyl), -aryl, —C1-C8 alkyl-aryl, —C1-C8 alkyl-(C3-C8 carbocycle), —C3-C8 heterocycle and —C1-C8 alkyl-(C3-C8 heterocycle); or $R^2$ is an oxygen atom which forms a carbonyl unit (C=O) with the carbon atom to which it is attached and a hydrogen atom on this carbon atom is replaced by one of the bonds in the (C=O) double bond; each $R^3$ is independently selected from the group consisting of H, OH, -aryl and C3-C8 heterocycle; $R^1$ is selected from the group consisting —H, —OH, —NH$_2$, —NHR$^5$, —N(R$^5$)$_2$, —C1-C8 alkyl, —C3-C8 carbocycle, —O—(C1-C8 alkyl), -aryl, —C1-C8 alkyl-aryl, —C1-C8 alkyl-(C3-C8 carbocycle), C3-C8 heterocycle and —C1-C8 alkyl-(C3-C8 heterocycle),

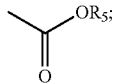

and each $R^5$ is independently —H or —C1-C8 alkyl.

Another aspect of the invention relates to compound having the structure:

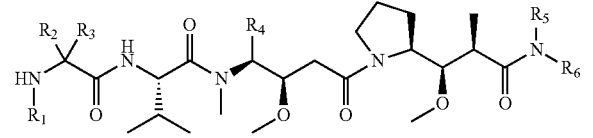

$R_1$ is H, C1-C8 alkyl;

$R_2$ is C1-C8 alkyl, C1-C8 alkyloxy, C3-C8 carbocycle, aryl, C3-C8 heterocycle, or C1-C8 haloalkyl;

$R_3$ is C1-C8 alkyl, C1-C8 alkyloxy, C3-C8 carbocycle, aryl, C3-C8 heterocycle, or C1-C8 haloalkyl; or $R_2$ and $R_3$ form a C3-C8 carbocycle or a C3-C8 heterocycle;

$R_4$ is H, C3-C8 carbocycle, aryl, C1 to C8 alkyl, or substituted alkyl, with the proviso that $R_4$ is not sec butyl;

$R_5$ is H;

$R_6$ is

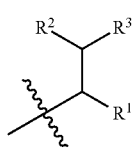

Where
$R^1$ is methyl,

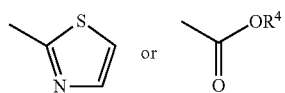

$R^2$ is aryl
$R^3$ is H or OH
$R^4$ is H, methyl or tert-butyl.

Another aspect of the invention relates to a compound having the structure:

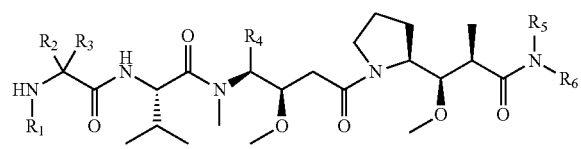

$R_1$ is H, methyl;
$R_2$ is methyl;
$R_3$ is methyl;
$R_4$ is C3-C6 carbocycle, aryl, C1 to C5 alkyl, with the proviso that $R_4$ is not sec butyl;
$R_5$ is H;
$R_6$ is

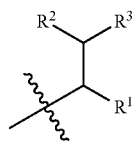

where
$R^1$ is methyl,

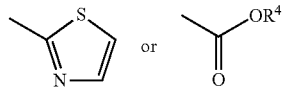

$R^2$ is aryl
$R^3$ is H or OH
$R^4$ is H, methyl or tert-butyl.

Another aspect of the invention relates to compound having the structure:

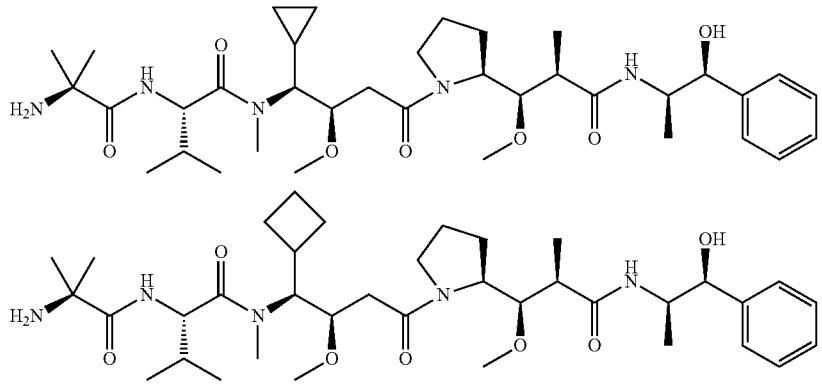

-continued
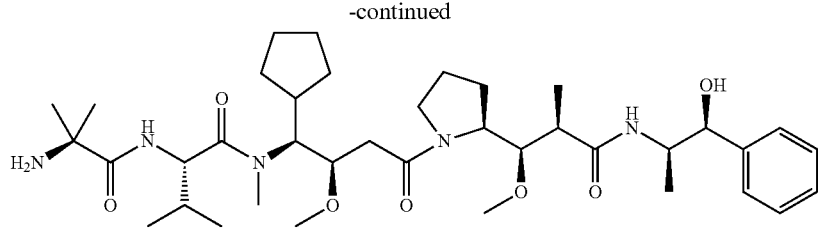
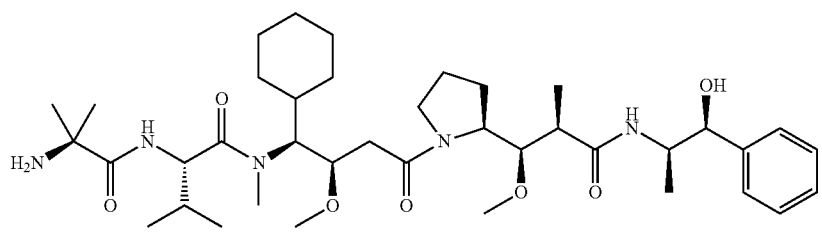
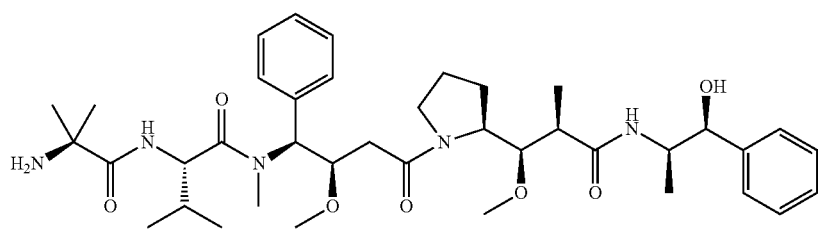
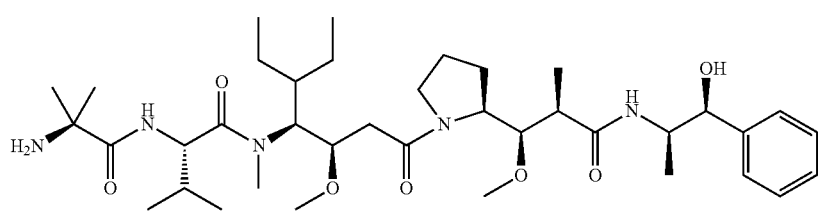
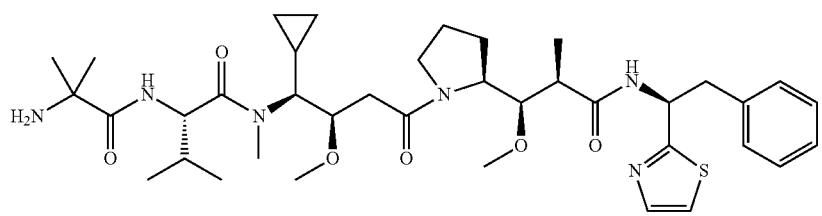
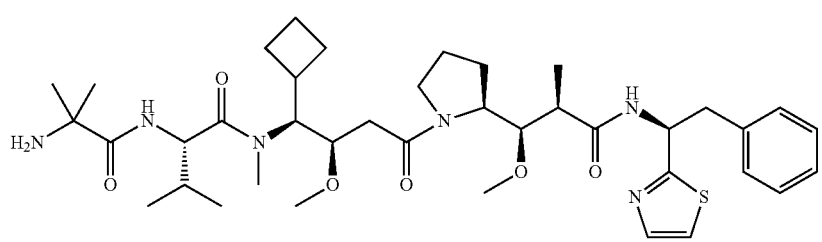
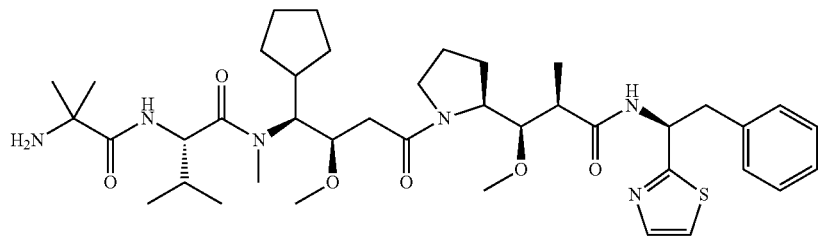

-continued
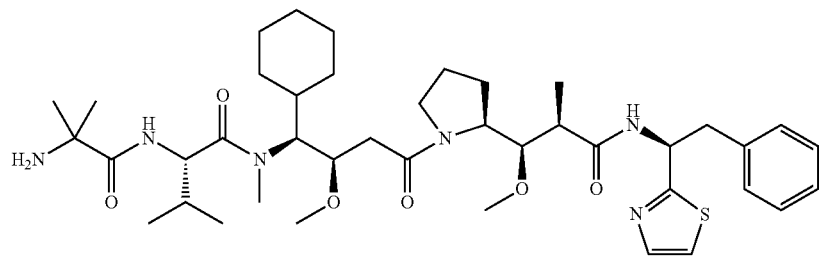
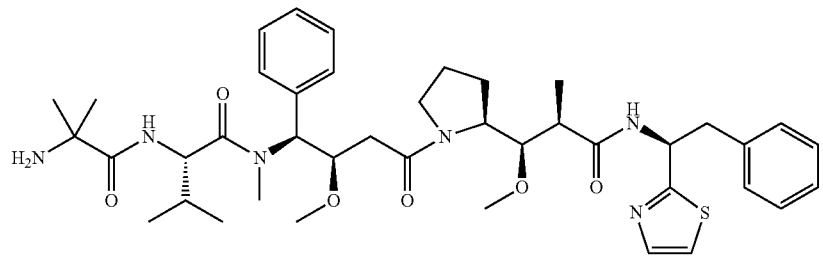
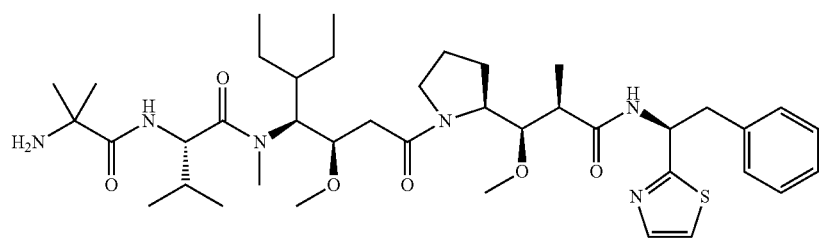
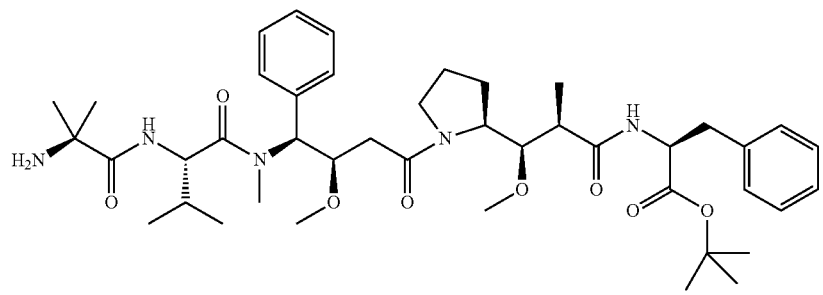
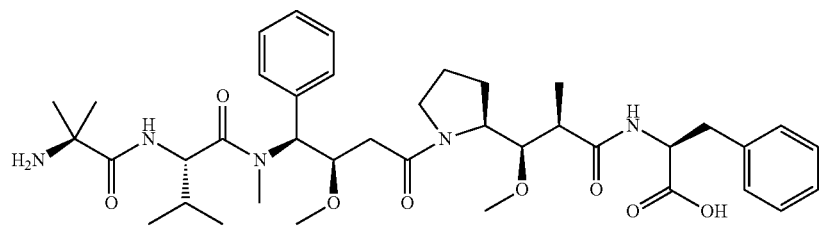
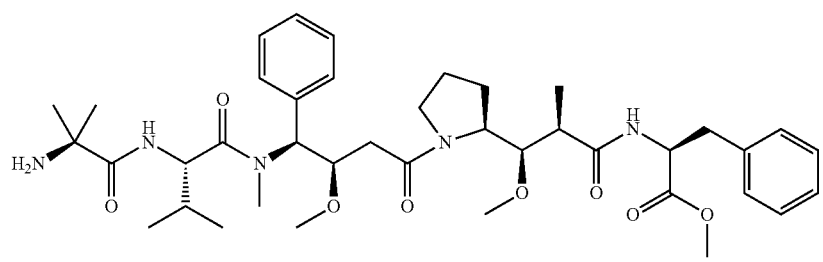

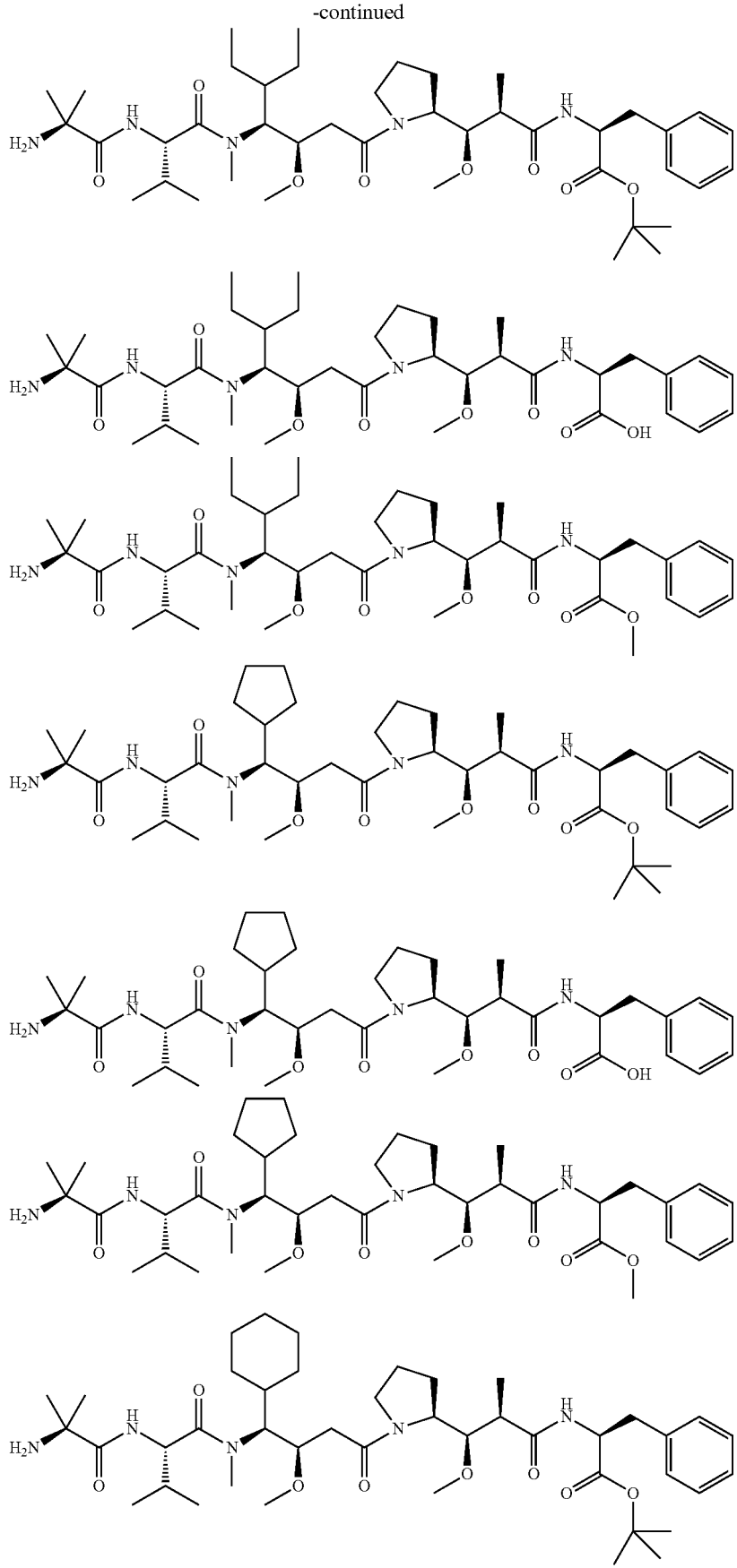

-continued
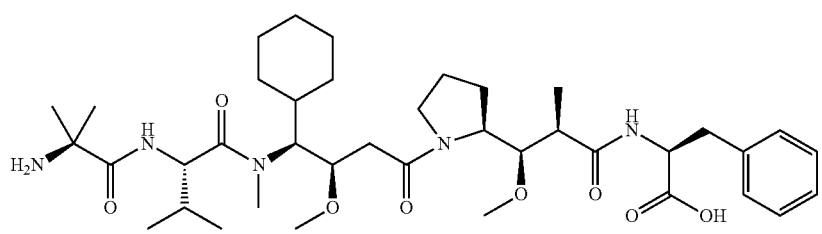
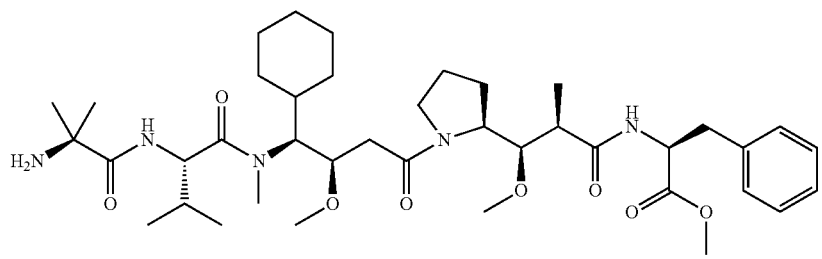
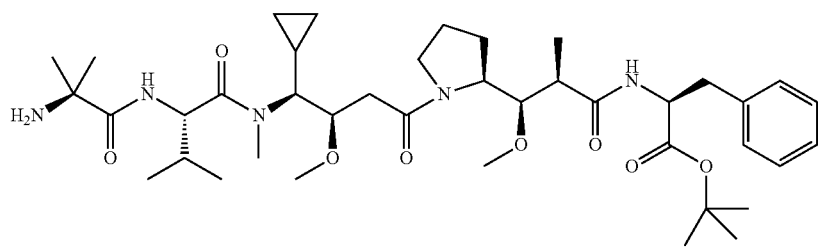
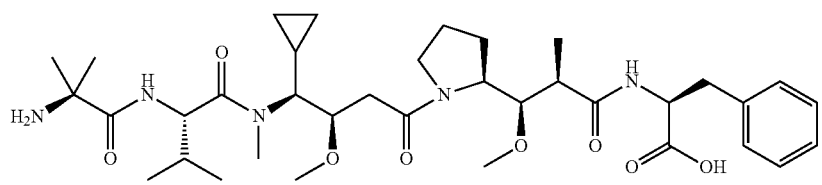
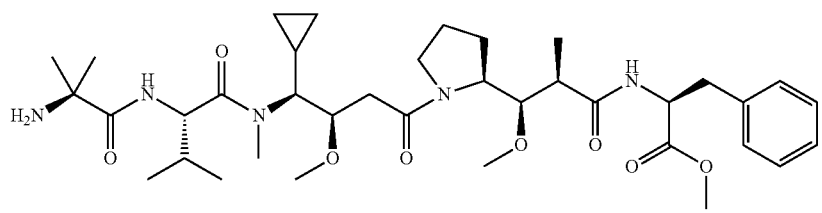
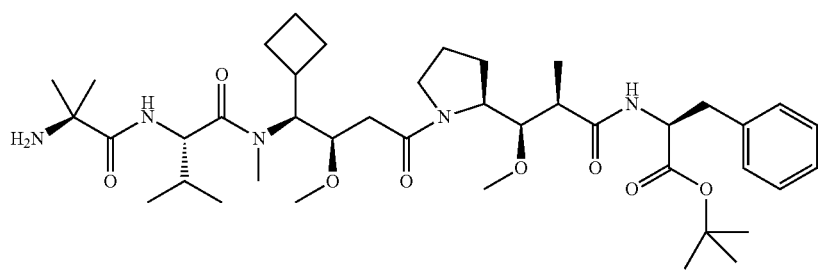
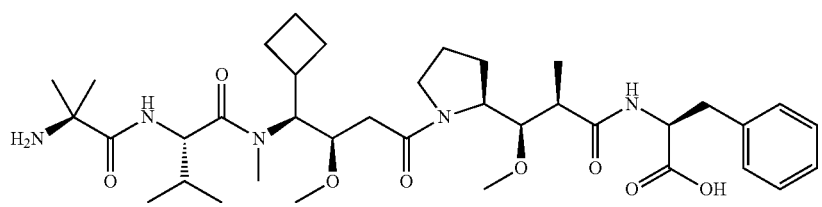

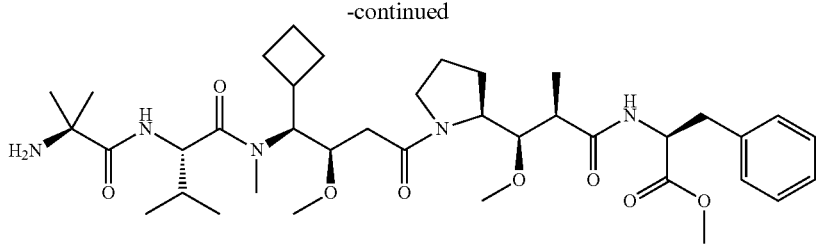

Another aspect of the invention relates to a drug-linker compound or pharmaceutically acceptable salt of a drug-linker having a formula:

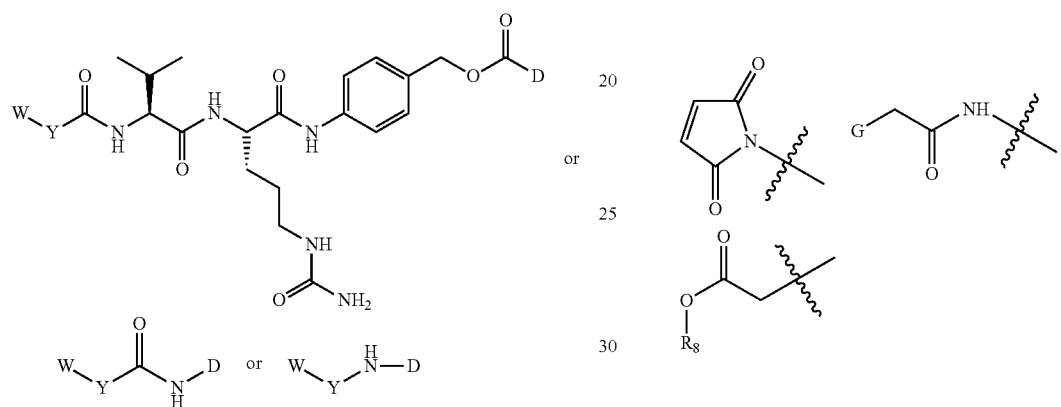

D is a drug, according claim 1, 2, 3 or 4;
Y is —C2-C20 alkylene-, —C2-C20 heteroalkylene-; —C3-C8 carbocycle-, -arylene-, —C3-C8 heterocyclo-, —O—C10 alkylene-(C3-C8-carbocyclo0-, —(C3-C8-carbocyclo-)-O—C10 alkylene-, —O—C10 alkylene-(C3-C8 heterocyclo)- or —(C3-C8 heterocyclo)-O—C10 alkylene-;
W is

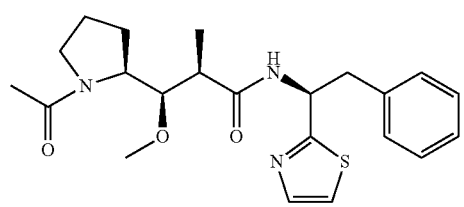

G is halogen, —OH, —SH or —S—C1-C6 alkyl; and
R8 is H, C1 to C10 alkyl.

Another aspect of the invention relates to drug-linker compounds having the following structures:

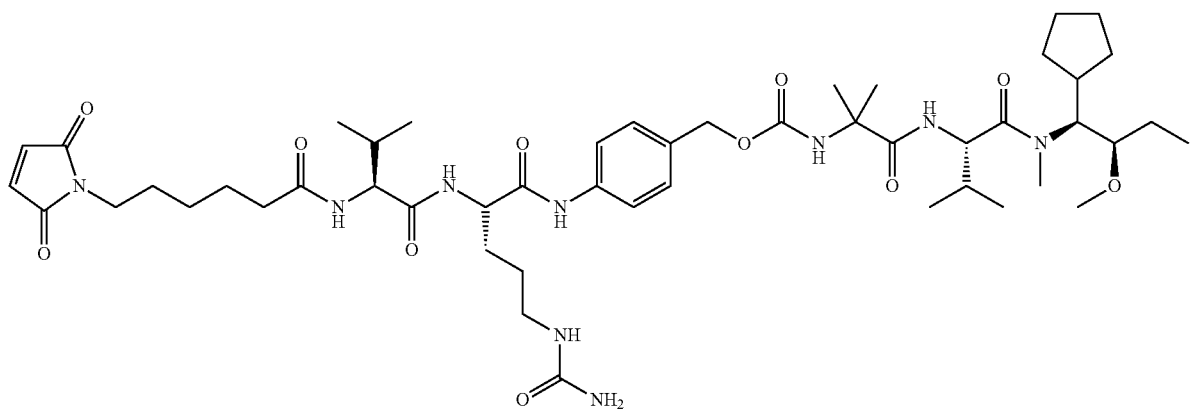

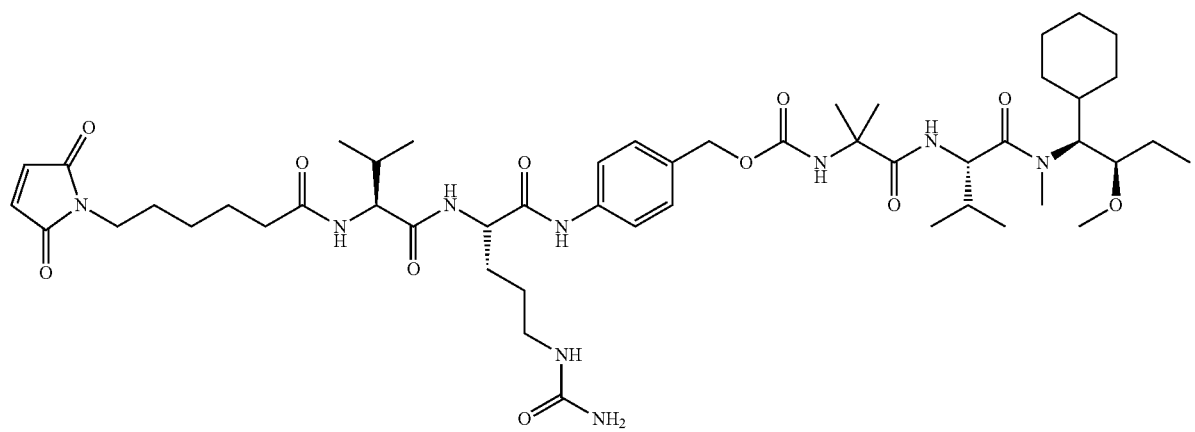
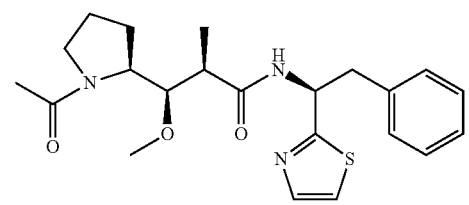
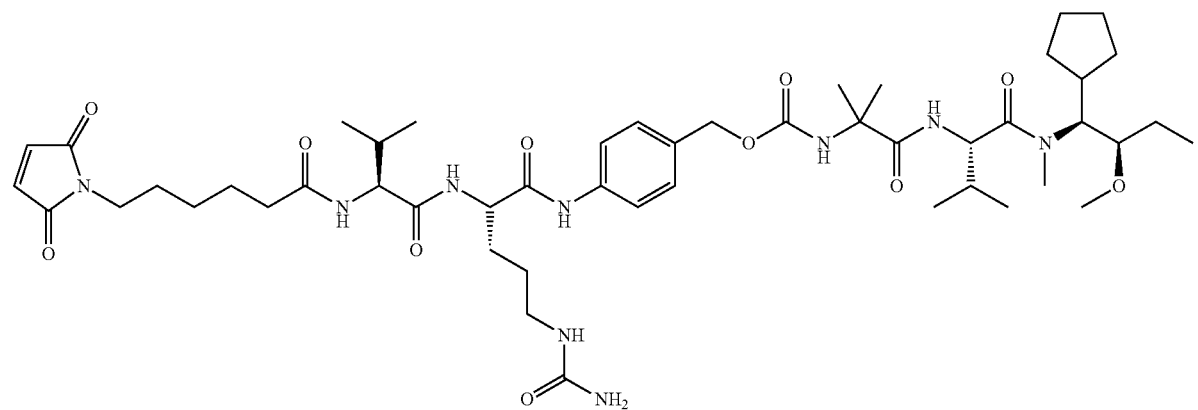
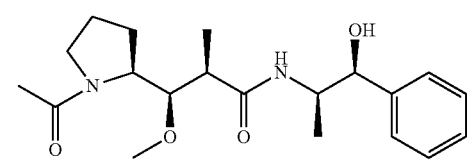
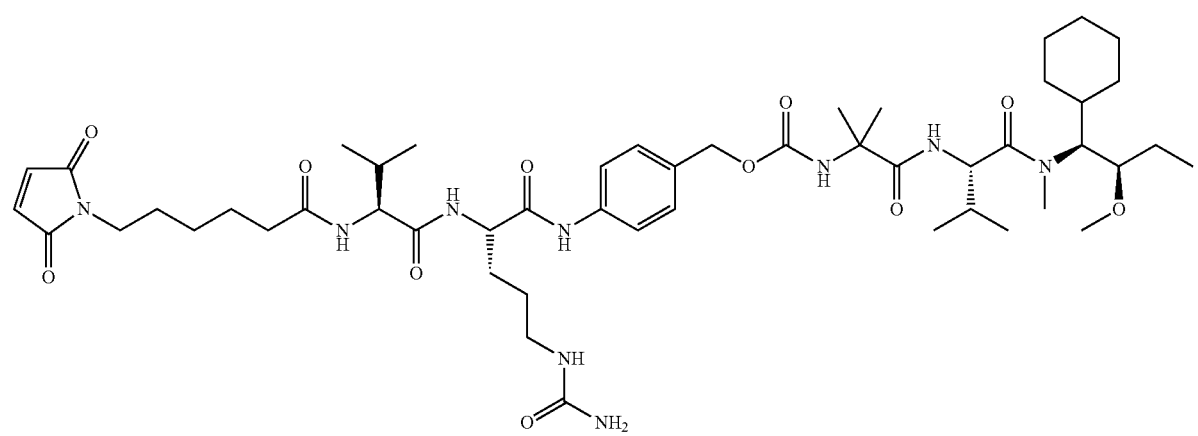

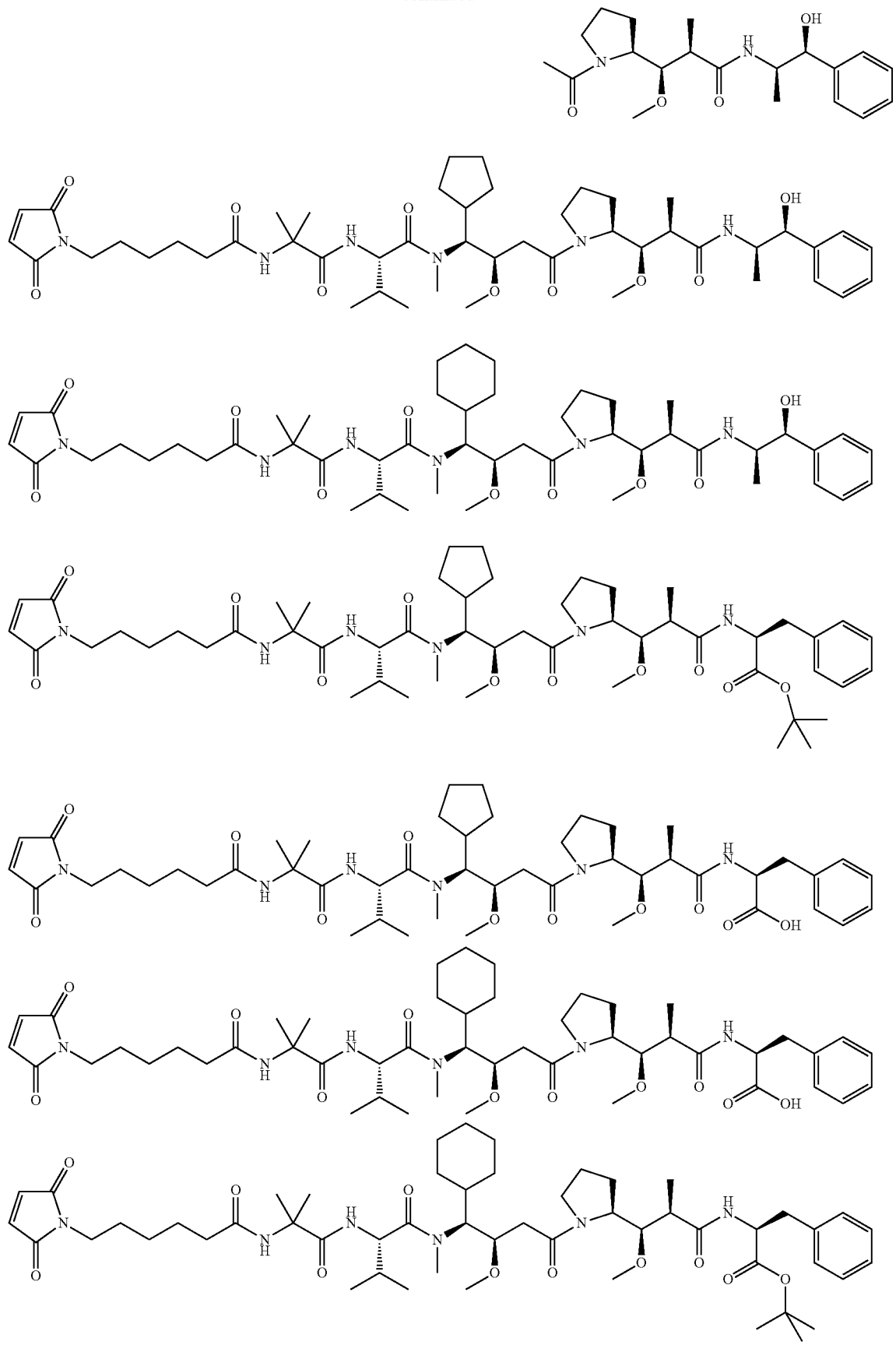

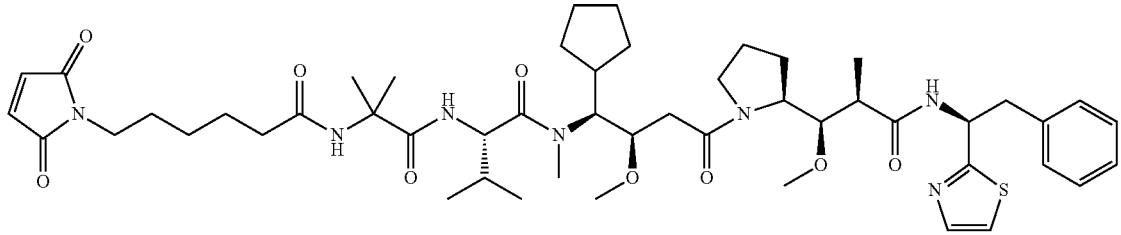
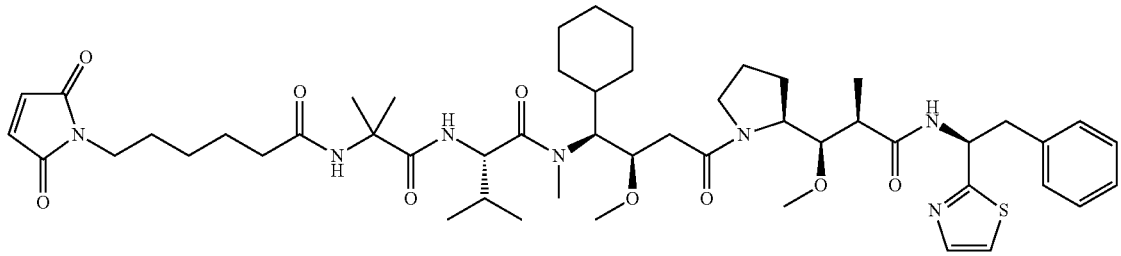
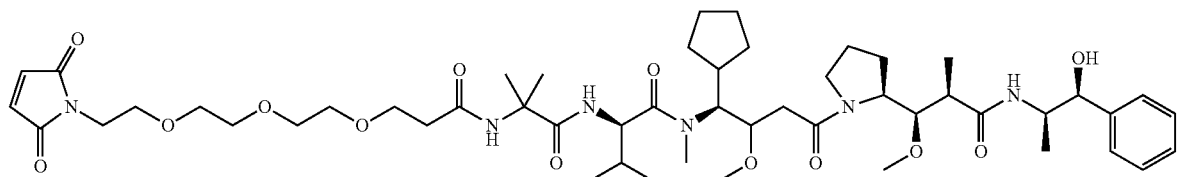
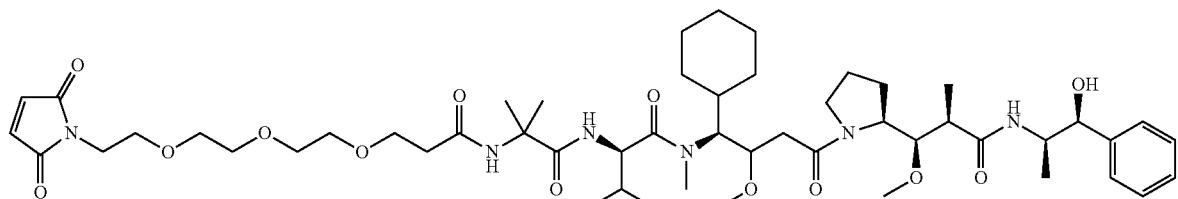
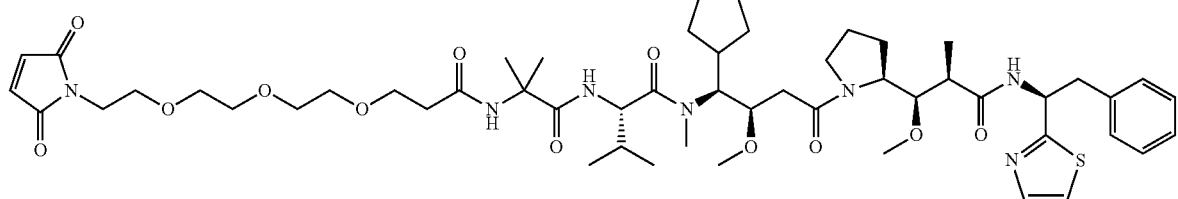
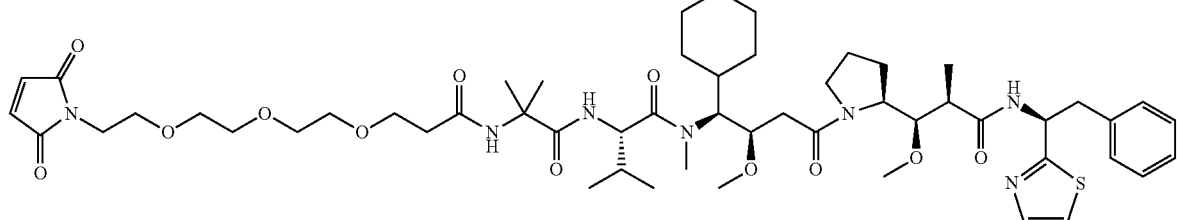
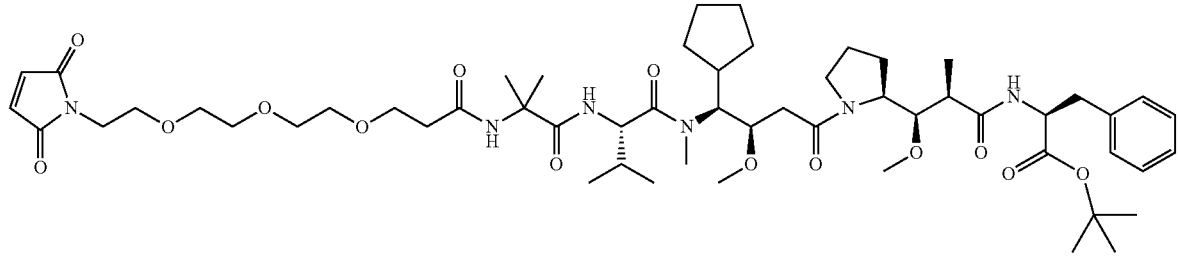

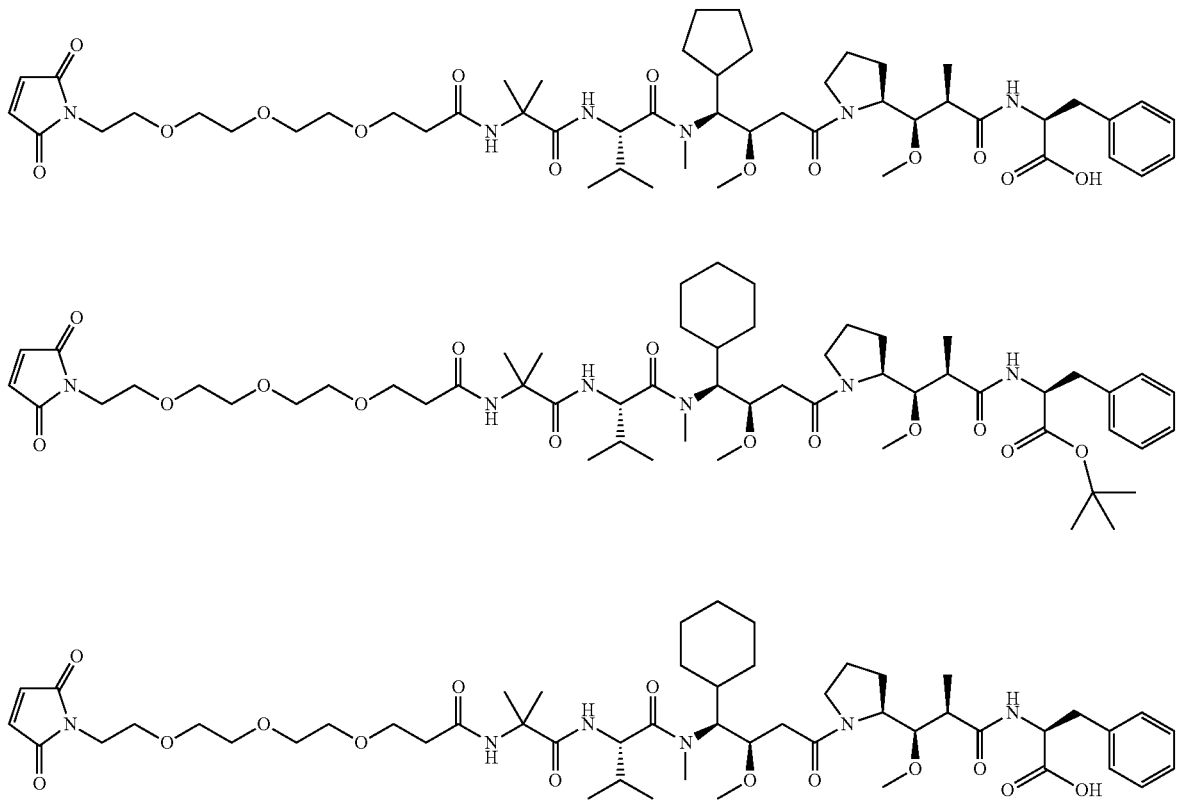

Another aspect of the invention relates to a drug conjugate having the following structures:

A-L-D)$_n$, where
A is a ligand, including antibody, peptide and small molecule ligand, as defined above,
L is a linker and
D is a drug, as discussed above, or 4; n is 1 to 4; the linker is directly linked to a drug or through a spacer; and A is attached to the linker L via the thiol group of cysteine or amino group of lysine of the antibody or ligand.

Another aspect of the invention relates to a drug conjugate or pharmaceutically acceptable salt of a drug conjugate has a formula:

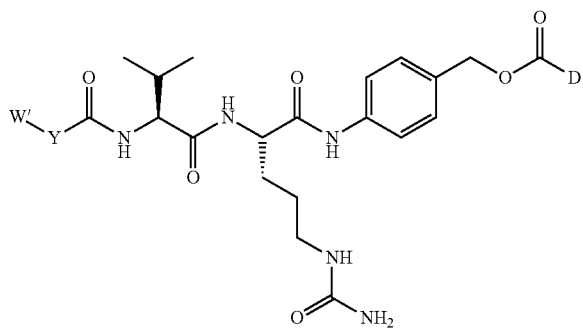

-continued

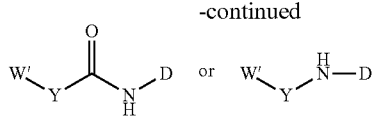

D is a drug, according to claim 1, 2 or 3 or 4.
Y is —C2-C20 alkylene-, —C2-C20 heteroalkylene-; —C3-C8 carbocycle-, -arylene-, —C3-C8 heterocyclo-, —O—C10 alkylene-(C3-C8-carbocyclo0-, —(C3-C8-carbocyclo-)-O—C10 alkylene-, —O—C10 alkylene-(C3-C8 heterocyclo)- or —(C3-C8 heterocyclo)-O—C10 alkylene-;
W' is

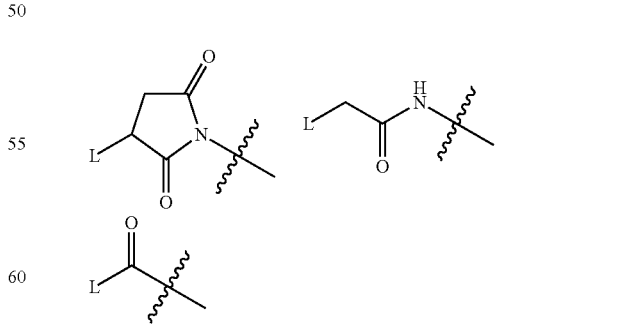

L is an antibody, peptide or small molecule ligand.
Another aspect of the invention relates to a drug conjugate or pharmaceutically acceptable salt of a drug conjugate has formulas:

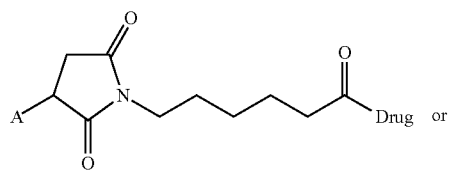
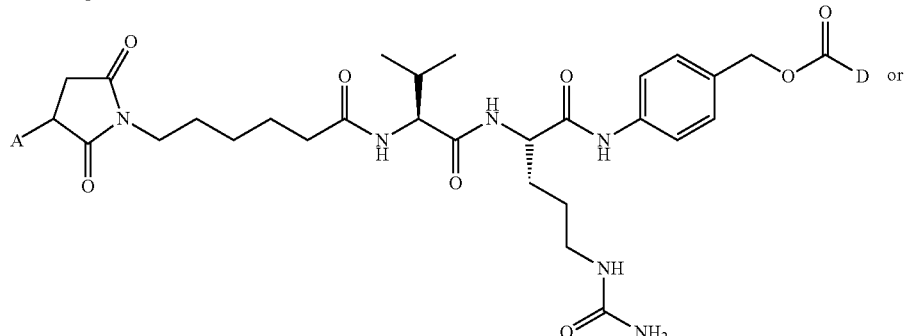
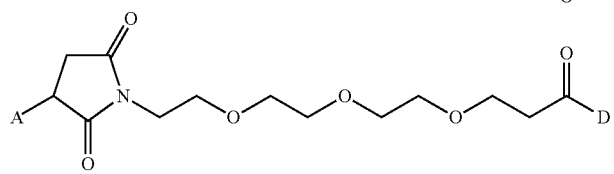
where D is a drug as discussed above, and A is an antibody.
Another aspect of the invention relates to a drug conjugate or pharmaceutically acceptable salt of a drug conjugate having the formula:
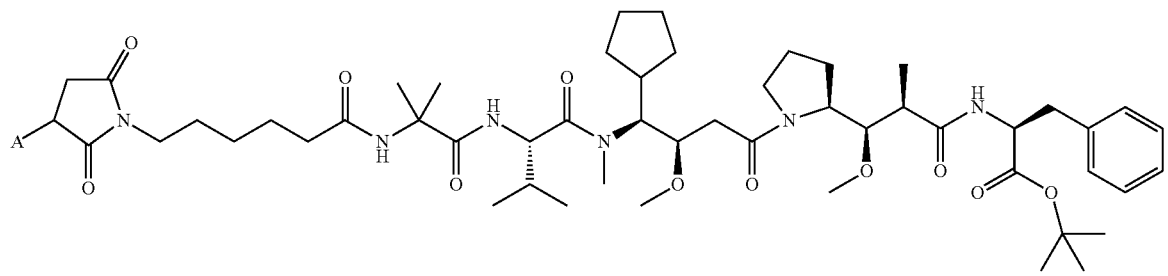
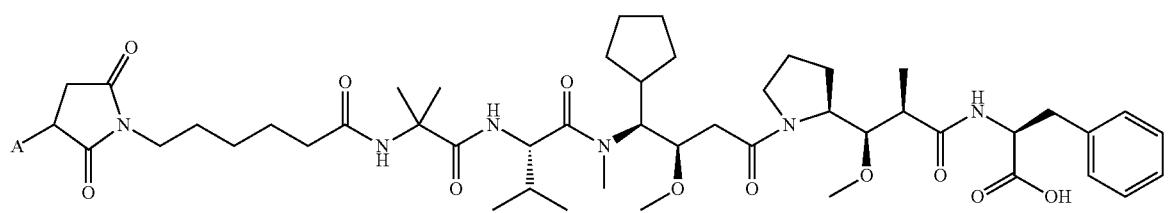
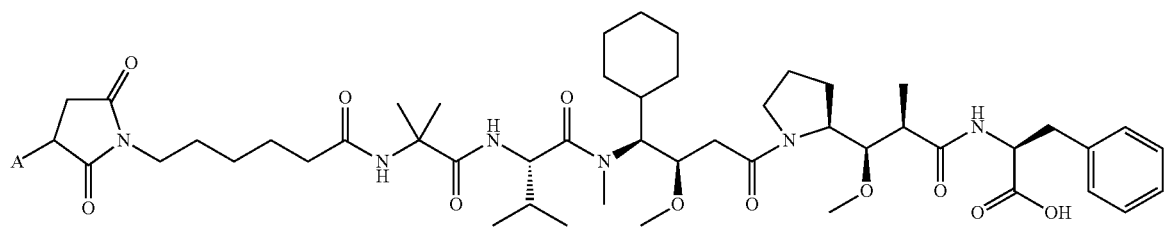

-continued
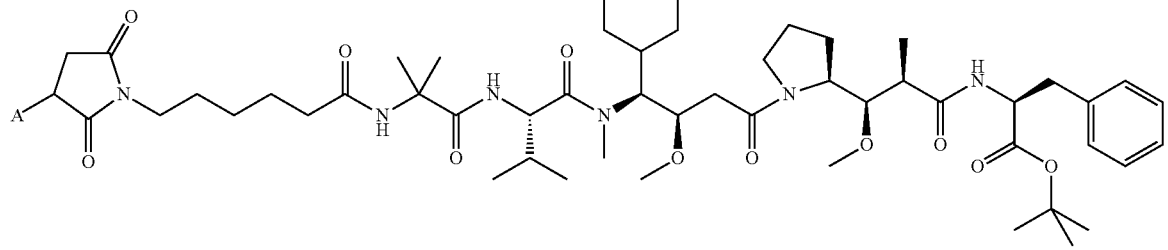
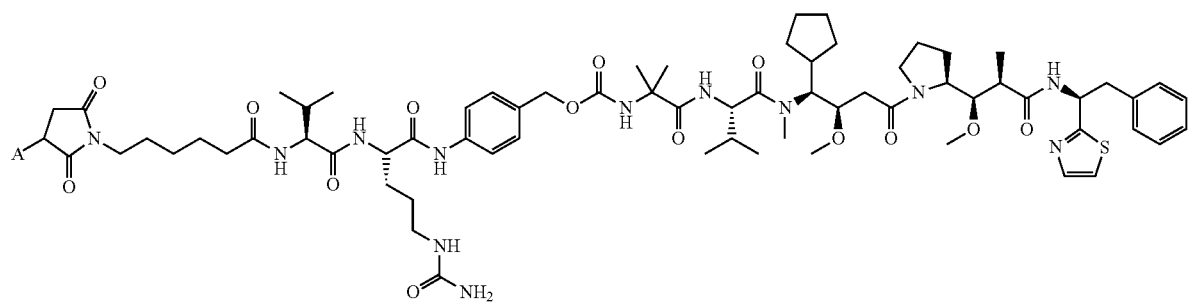
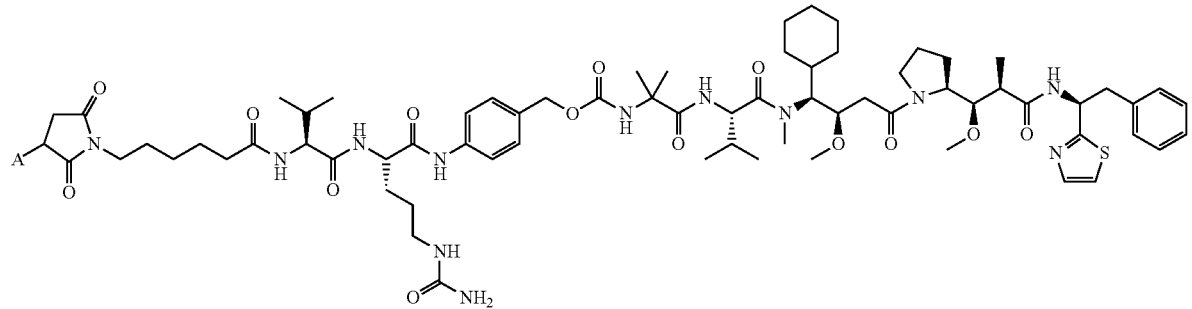
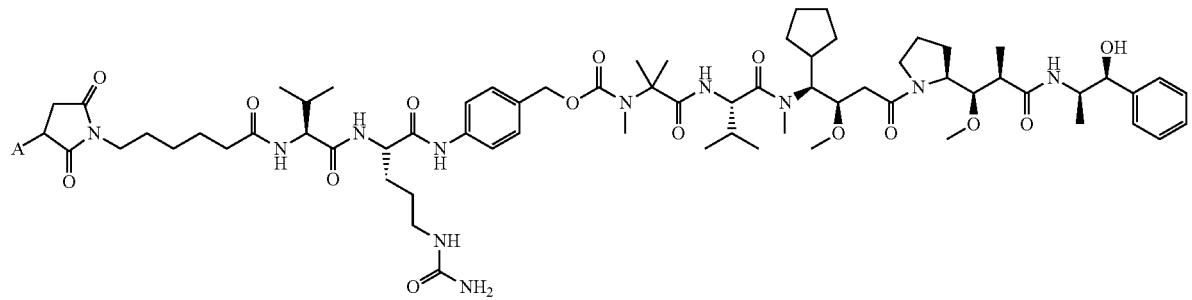
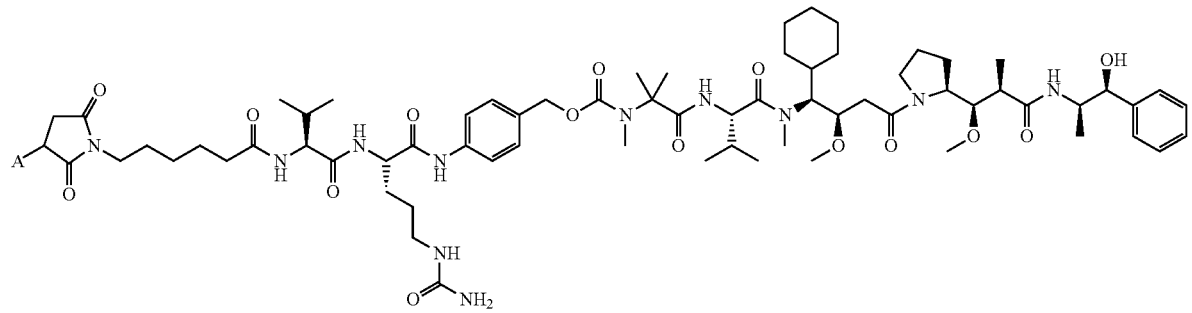

-continued
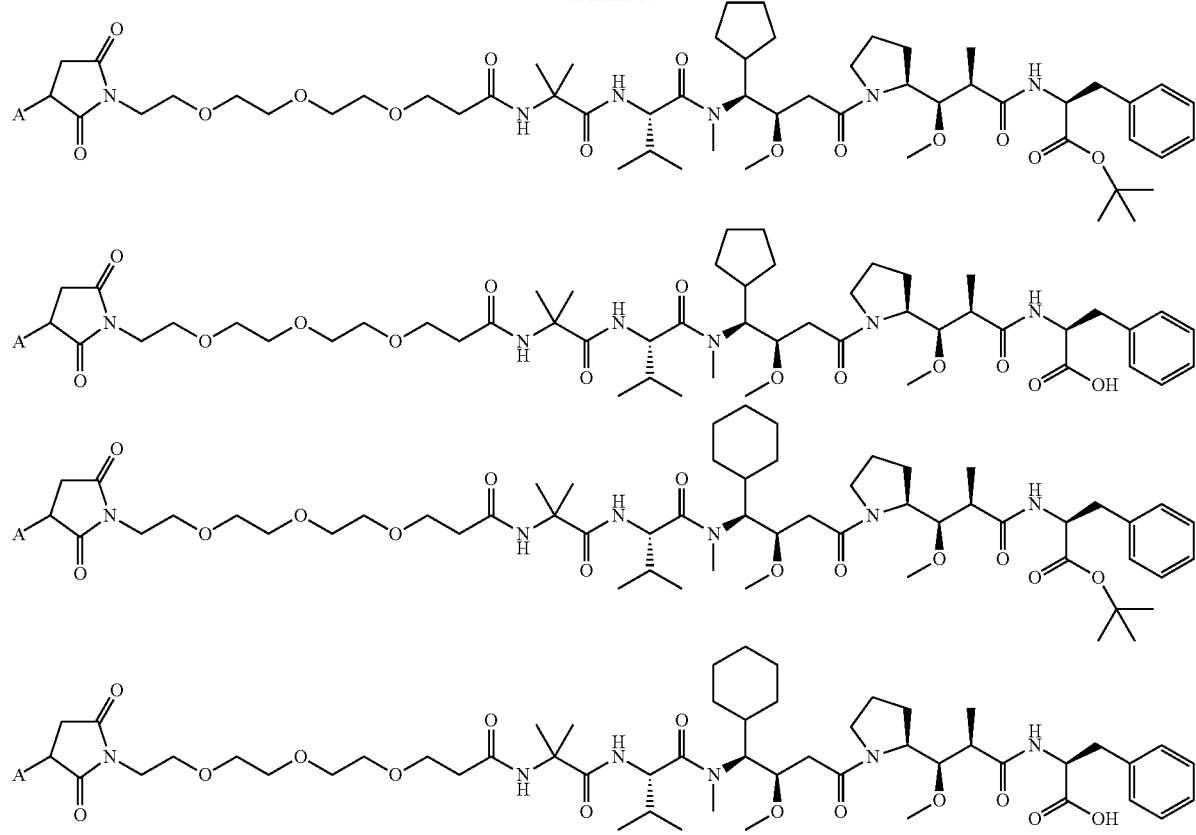
where A is an antibody
Structure Nomenclature
1).
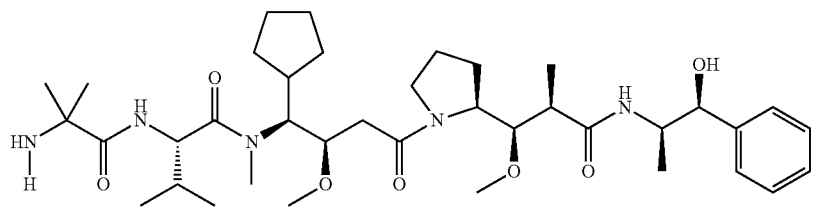
(S)-2-(2-amino-2-methylpropanamido)-N-((1S,2R)-1-cy-clopentyl-4-((S)-2-((1R,2R)-3-((1S,2R)-1-hydroxy-1-phenylpropan-2-ylamino)-1-methoxy-2-methyl-3-oxo propyl)pyrrolidin-1-yl)-2-m ethoxy-4-oxobutyl)-N,3-dimethylbutanamide (17) 2).
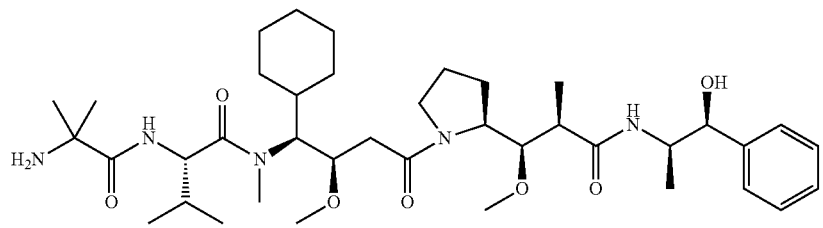

(S)-2-(2-amino-2-methylpropanamido)-N-((1S,2R)-1-cyclohexyl-4-((S)-2-((1R,2R)-3-((1S,2R)-1-hydroxy-1-phenylpropan-2-ylamino)-1-methoxy-2-methyl-3-oxopropyl)pyrroli-din-1-yl)-2-methoxy-4-oxobutyl)-N,3-dimethylbutanamide (18)

3).

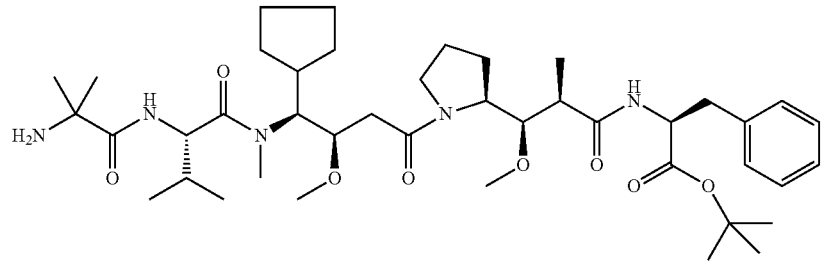

(S)-tert-butyl2-((2R,3R)-3-((S)-1-((3R,4S)-4-((S)-2-(2-amino-2-methylpropanamido)-N,3-dimethylbutanamido)-4-cyclopentyl-3-methoxybutanoyl)pyrrolidin-2-yl)-3-methoxy-2-methylpropanamido)-3-phenylpropanoate (21)

4).

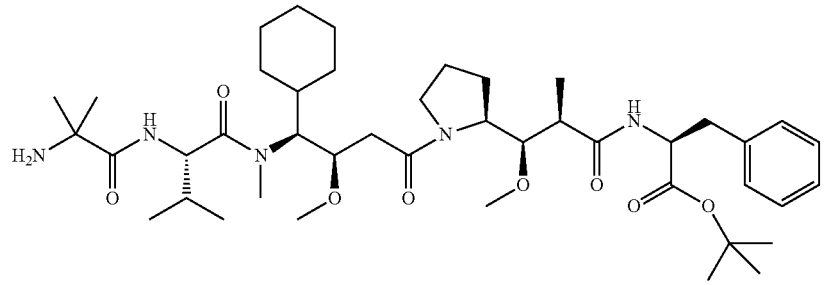

(S)-tert-butyl-2-((2R,3R)-3-((S)-1-((3R,4S)-4-((S)-2-(2-amino-2-methylpropanamido)-N,3-di methylbutanamido)-4-cyclohexyl-3-methoxybutanoyl)pyrrolidin-2-yl)-3-methoxy-2-methylpropanamido)-3-phenylpropanoate (22)

5).

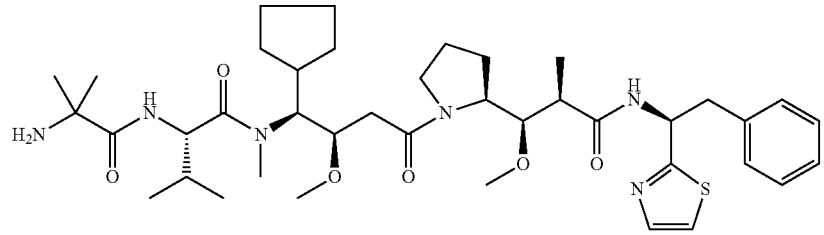

(S)-2-(2-amino-2-methylpropanamido)-N-((1S,2R)-1-cyclohexyl-2-methoxy-4-((S)-2-((1R,2R)-1-methoxy-2-methyl-3-oxo-3-((S)-2-phenyl-1-(thiazol-2-yl)ethylamino)propyl)pyrrolidin-1-yl)-4-oxobutyl)-N,3-dimethylbutanamide (23) 6).

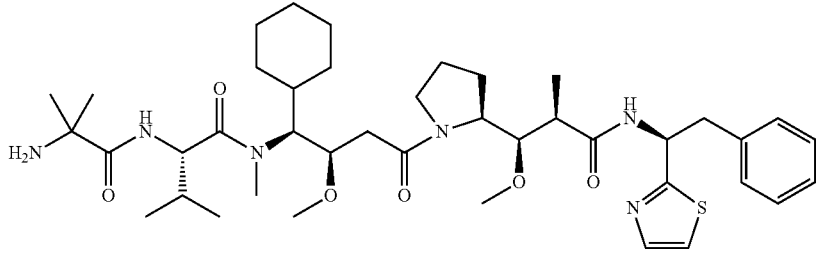

24

(S)-2-(2-amino-2-methylpropanamido)-N-((1S,2R)-1-cyclohexyl-2-methoxy-4-((S)-2-((1R,2R)-1-methoxy-2-methyl-3-oxo-3-((S)-2-phenyl-1-(thiazol-2-yl)ethylamino)propyl)pyrrolidin-1-yl)-4-oxobutyl)-N,3-dimethylbutanamide (24) 7).

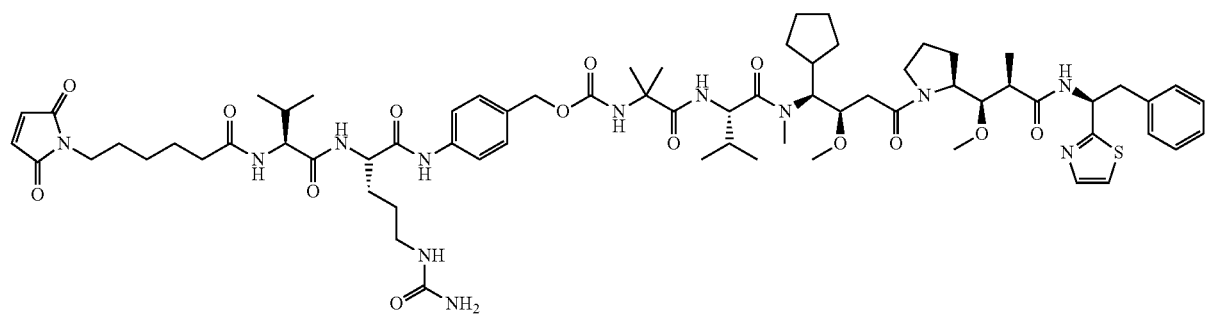

27

4-((S)-2-((S)-2-(6-(2,5-dioxo-2,5-dihydro-1H-pyrrol-1-yl)hexanamido)-3-methylbutanamido)-5-ureidopentanamido)benzyl 1-((S)-1-(((1S,2R)-1-cyclopentyl-2-methoxy-4-((S)-2-((1R,2R)-1-m ethoxy-2-methyl-3-oxo-3-((S)-2-phenyl-1-(thiazol-2-yl)ethylamino)propyl)pyrrolidin-1-yl)-4-oxobutyl)(methyl)amino)-3-methyl-1-oxobutan-2-ylamino)-2-methyl-1-oxopropan-2-ylcarbamate (27)

BRIEF DESCRIPTION OF DRAWINGS

FIG. 1A shows the IC50 curves of payload 18, IgG1-vc18 and H-vc18 against HCC1954;

FIG. 1B. shows the IC50 curves of payload 18, IgG1-vc18 and H-vc18 against SK-BR-3;

FIG. 1C. shows the IC50 the curves of payload 18, IgG1-vc18 and H-vc18 against MCF-7;

FIG. 2A. depicts the Selectivity between H-vc18 & IgG1-drug control against Her2 positive cancer cell lines HCC1954 and SK-BR-3;

FIG. 2B. depicts the Selectivity between Her2 positive cancer cell lines & MCF-7;

FIG. 2C. depicts the Efficiency ratio between free drugs vs ADCs against Cancer cell lines HCC 1954 and SK-BR-3.

DESCRIPTION OF EMBODIMENTS

Experimental $^{1}$H and $^{13}$C-NMR spectra were recorded on a 400 MHz Bruker spectrometer. Chemical shifts for NMR are expressed as parts per million (ppm, δ). Chloroform-d or dimethyl sulfoxide-$d_6$ was used as solvents when unspecified.

In general, reactions were monitored by thin layer chromatography (TLC), or high pressure liquid chromatography (HPLC) or liquid chromatography-mass spectrometry (LC-MS). HPLC is performed on an Agilent 1100 instrument. Conditions for analysis are as follows:

Method A:
Column: Phenomenexluna C18, 50×4.6 mm, 5μ, Mobile phase A: 0.1% trifluoroacetic acid in water (v/v); Mobile phase B: 0.1% trifluoroacetic acid in acetonitrile (v/v); Gradient: 5% B to 95% B over 4.5 minutes, then 95% B for 0.5 minute; Flow rate: 1.5 mL/min.; Temperature: 25° C.; Detection: DAD 210 nm and 254 nm.

Method B:
Column: Phenomenexluna C18, 250 mm×4.6 mm, 5 m, Mobile phase A: 0.1% trifluoroacetic acid in water (v/v); Mobile phase B: 0.1% trifluoroacetic acid in acetonitrile (v/v); Gradient: 10% B to 90% B over 20 minutes, then 90% B for 3 minute; Flow rate: 1.0 mL/min.: Temperature: 25° C.; Detection: DAD 210 nm and 254 nm.

Method C: Preparative HPLC-1:
Column: C18, 250 mm×40 mm, 5μ, Mobile phase A: 0.1% trifluoroacetic acid in water (v/v); Mobile phase B: 0.1% trifluoroacetic acid in acetonitrile (v/v); Gradient: 10% B over 10 min, 10% B to 90% B over 120 minutes, then 90% B for 10 minute; Flowrate: 10.0 mL/min.: Temperature: 25° C.; Detection: DAD 220 nm or 254 nm.

Method D: Preparative HPLC-2:
Column: C18, 250 mm×40 mm, 5μ, Mobile phase A: water; Mobile phase B: acetonitrile; Gradient: 10% B over 10 min, 10% B to 90% B over 120 minutes, then 90% B for 10 minute; Flow rate: 10 mL/min.: Temperature: 25° C.; Detection: DAD 220 nm or 254 nm.

Mass spectrometry data is obtained by an Agilent G1946D liquid chromatography-mass spectrometry (LC-MS). Conditions for analysis is as follows: Column: Phenomenexluna C18, 150 mm×2.0 mm, Mobile phase A: 0.05% formic acid in water (v/v); Mobile phase B: 0.05% formic acid in acetonitrile (v/v); Gradient: 10% B to 90% B over 10 minutes, then 90% B for 2 minute; Flow rate: 0.4 mL/min.: Temperature: 25° C.; Detection: DAD 210 nm and 254 nm; Mass detector: Electron Spray Ionization (ESI), positive and negative. Mass range: 100 to 1000 m/z or 500 to 1500 m/z.

Procedure for Conjugating Antibodies with Linker-Drugs

The conjugation of antibodies with linker-drugs used a modified procedure as that of US 20050238649A1 and US20130129753. The DAR values (drug antibody ratio) were measured using a similar procedure disclosed in US 20050238649A1.

The mc-Val-Cit-paraaminobenzylcarbamate-drug (vcMMAE type) or mc-drug was performed as described (Doronina S O, et al, *Nat. Biotechnology* 2003, 21, 778-84). Herceptin and isotope-control human (IgG1) in PSB containing 50 mM borate buffer, PH 8.0 were treated with dithiothreitol (DTT) (10 mM final) at 37° C. for 30 minutes under nitrogen. After cool to 0° C., the antibody solution was passed through a G-25 column eluted with PBS buffer and the fractions containing the reduced antibody was collected. To above reduced antibody was added drug molecule (3.6 eqmol) in DMA solution (5 mM) and incubated at 25° C. for 1 hour. After cool to 0° C., the ADC solution was passed a G-25 column eluted with PBS buffer. The concentration of antibody was measured using UV-VIS spectrophotometer (Shimazu, Japan).

The concentration of antibody cysteine thiols was determined by reacting with 5,5'-dithio-bis-(2-nitrobenzoicacid) (DTND).

In Vitro Cell Assay:

In vitro cell assay is performed in a 96 well micro titer plate. Human tumor cell lines Hela, A549, MCF-7, HCC-1954 and SK-BR-3 are obtained from ATCC (American Type Culture Collection).

Cell Seeding.

The cells were harvested respectively during the logarithmic growth period and counted with hemocytometer. The cell viability was over 98% by trypan blue exclusion. 90 μl of cell suspensions were added in to 96-well plates, the final cell density was reached to 3000 cells/well. Plates were incubated for 96 hours at 37° C., and 5% CO2.

Drug Addition and T0 Plate Reading.

To each well was added 10 μL of DMSO diluted compound (10×). For the sentinel base T0 plate, to each well was added 100 μL Cell Titer Gloand the luminescence signals with Envision reading were recorded.

Plate Reading and Data Analysis.

After 5 days incubation, cells are checked under the microscope to make sure that the cells in cell control wells are healthy. Plates are read with Envision after adding Cell Titer Glo to each well. IC$_{50}$ values were calculated using GraphPad Prism 5.

1. Preparation of (S)—N-((1S,2R)-1-cyclopentyl-4-((S)-2-((1R,2R)-3-((1S,2R)-1-hydroxy-1-phenylpropan-2-ylamino)-1-methoxy-2-methyl-3-oxopropyl)pyrrolidin-1-yl)-2-methoxy-4-oxobutyl)-N,3-dimethyl-2-((S)-3-methyl-2-(methylamino)butanamido)butanamide (17)

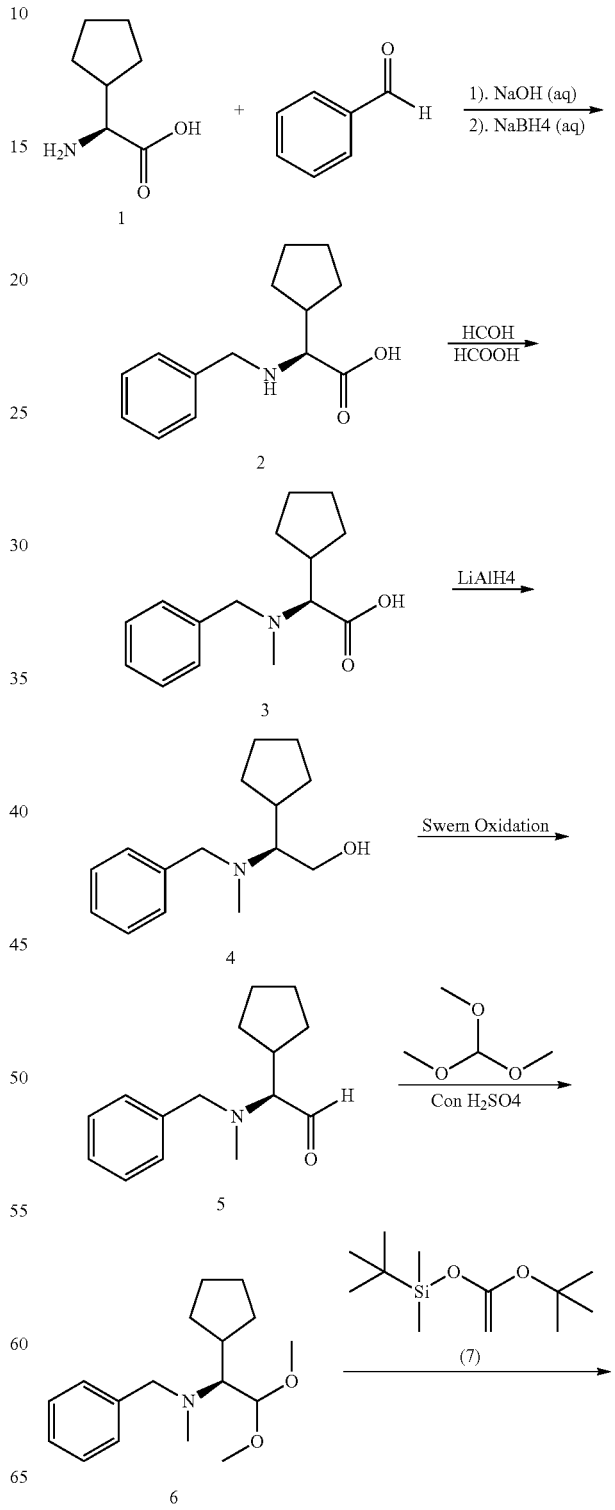

-continued

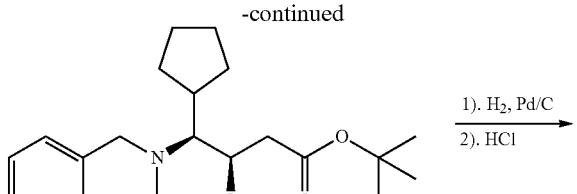
8

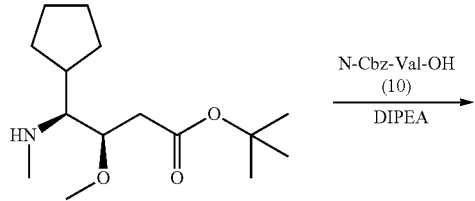
9

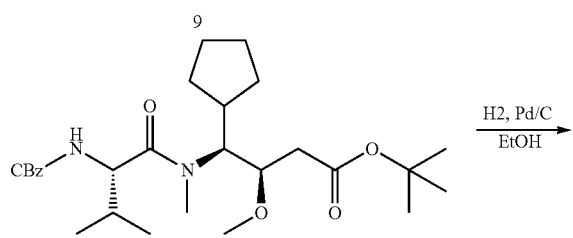
11

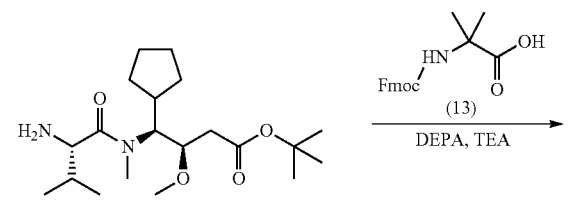
12

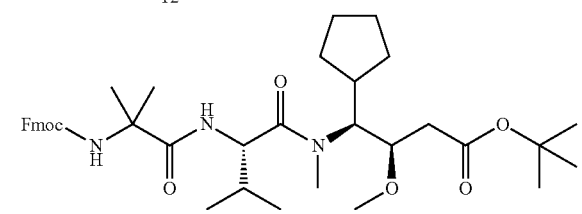
14

Step 1

Synthesis of (S)-2-(benzylamino)-2-cyclopropylacetic acid (2)

(S)-2-amino-2-cyclopentylacetic acid (1) (66.0, 0.46 mol, 1.0 eq) was added in portions into 2N NaOH (230 mL, 0.46 mol, 1.0 eq) with stirring. After complete dissolution of the amino acid, benzaldehyde (49.0 g, 0.46 mol, 1.0 eq) was added all at once. The reaction mixture was allowed to stir at room temperature for 1 h. Sodium borohydride (17.5 g, 0.46 mol, 1.0 eq) was added slowly in portions at 0° C., and the reaction mixture was stirred at room temperature for 4 h. Then the reaction mixture was diluted with water (250 mL) and extracted twice with diethyl ether (250 mL). The clear aqueous layer was neutralized with 4N HCl (aq) to pH=7 and the white suspension were stirred at rt for 0.5 h. After filtration, the solid was washed with water (250 mL), the filter cake was dried to yield the product 2 (66 g, 59%) as a white solid.
$^1$H-NMR (300 MHz, DMSO-d6): δ 7.2-57.34 (m, 5H), 3.59-3.89 (m, 2H), 2.88 (d, J=7.2 Hz, 1H), 1.99~2.07 (m, 1H), 1.35~1.68 (m. 8H); LC-MS: m/z 234 [M+H$^+$]$^+$.

Step 2

Synthesis of (S)-2-(benzyl(methyl)amino)-2-cyclopentylacetic acid (3)

To a solution of (S)-2-(benzylamino)-2-cyclopropylacetic acid (2) (226.0 g, 0.11 mol, 1.0 eq) in formic acid (15.4 g, 0.33 mol, 3.0 eq) was added an aqueous solution of formaldehyde (36.5%, 13.6 g, 0.16 mol, 1.5 eq). The reaction mixture was heated to 90° C. for 2 h. After cooled, the solvent was evaporated under reduced pressure and the residue was diluted with acetone (200 mL) under stirring at 0° C., the precipitate was filtered, washed with cold acetone (50 mL) and dried to afford the product 3 (23.5 g, 85%) as a white solid. $^1$H-NMR (300 Hz, DMSO-d6): δ 7.23~7.30 (m, 5H), 3.74 (d, J=13.5 Hz, 1H), 3.47 (d, J=13.8 Hz, 1H), 2.85 (d, J=11.1 Hz, 1H), 2.16 (m, 1H), 2.09 (m, 3H), 1.07-1.49 (m, 8H); LC-MS: m/z 248 [M+1]$^+$.

Step 3

Synthesis of (S)-2-(benzyl(methyl)amino)-2-cyclopentylethanol (4)

To a suspension of lithium aluminum hydride (2.3 g, 61.0 mmol, 1.5 eq) in anhydrous THF (200 mL) at 0° C. was added (S)-2-(benzyl(methyl)amino)-2-cyclopentylacetic acid (3) (10.0 g, 40.0 mmol, 1.0 eq) in portions at 0° C. The reaction mixture was stirred at room temperature for 2 h followed by heating to reflux for 2 h, After cooled, water (2.5 mL) was added at 0° C. followed by 5% NaOH (2.5 mL, aq). The suspension formed was filtered and washed with ethyl acetate (50 mL). Water (250 mL) was then added to the filtrate, which was extracted with ethyl acetate. The organic layer was washed with brine, dried over sodium sulphate and evaporated in vacuo to give the product 4 as an oil (quant); LC-MS: m/z 234 [M+H$^+$]$^+$

Step 4

Synthesis of (S)-2-(benzyl(methyl)amino)-2-cyclopentylacetaldehyde (5)

To a solution of oxalyl chloride (8.7 g, 68.5 mmol, 2.0 eq) in anhydrous dichloromethane (200 mL) was added drop-wise a solution of DMSO (10.7 g, 137 mmol, 4.0 eq) in anhydrous dichloromethane (20 mL) at −78° C. under nitrogen. After 1 hour, a solution of (S)-2-(benzyl(methyl)amino)-2-cyclopentylethanol (4) (8.0 g, 34.3 mmol, 1.0 eq) in anhydrous dichloromethane (30 mL) was added drop-wise at −78° C. The reaction mixture was allowed to stir for another 1 hour at −78° C. Then triethylamine (27.8 g, 274 mmol, 8.0 eq) was added drop-wise at −78° C. After the addition the reaction mixture was warmed to 0° C. under stirring. After 30 min at 0° C., water (250 mL) was added into the reaction solution and the organic phase was washed with brine, dried over sodium sulphate and concentrated in vacuo to give the product 5 as an oil (quant); LC-MS: m/z 232 [M+H$^+$]$^+$.

Step 5

Synthesis of (S)—N-benzyl-1-cyclopentyl-2,2-dimethoxy-N-methylethanamine (6)

To a solution of (S)-2-(benzyl(methyl)amino)-2-cyclopentylacetaldehyde (7.9 g, 34 mmol, 1.0 eq) in MeOH (200 mL) was added concentrated $H_2SO_4$ (12.5 g, 127 mmol, 3.7 eq) drop-wise at 0° C. The reaction mixture was stirred for 10 min, then trimethylorthoformate was added (33 g, 311 mmol, 9.0 eq.) at 0° C. The reaction mixture was stirred at room temperature for 1 hour, and then heated to reflux for overnight. After cooled, the solvent was evaporated under reduced pressure, and the obtained residue was poured into sat $NaHCO_3$ (300 mL, aq), extracted with ethyl acetate (300 mL). The organic layer was washed with brine, dried over sodium sulphate and evaporated to give a residue, which was purified by column chromatography on silica to yield the product 6 (8.6 g, 90% for two steps) as a light color oil.

$^1$H-NMR (300 Hz, $CDCl_3$): δ 7.23~7.38 (m, 5H), 4.40 (d, J=3.6 Hz, 1H), 3.91 (d, J=14.1 Hz, 1H), 3.73 (d, J=14.1 Hz, 1H), 3.44 (s, 6H), 2.54~2.58 (m, 1H), 2.32 (s, 3H), 2.16-2.19 (m, 1H), 0.10-1.95 (m, 8H); LC-MS: m/z 278 $[M+H^+]^+$

Step 6

Synthesis of (3R,4S)-tert-butyl-4-(benzyl(methyl)amino)-4-cyclopentyl-3-methoxybutanoate (8)

To (1-tert-butoxyvinyloxy)(tert-butyl)dimethylsilane (7) (9.9 g, 43.0 mmol) in dichloromethane (80 mL) was added (S)—N-benzyl-1-cyclopentyl-2,2-dimethoxy-(S)—N-benzyl-1-cyclopentyl-2,2-dimethoxy-N-methylethanamine (6) (8.0 g, 28.8 mmol) followed by a solution of $BF_3$. ether (3.6 mL) in DMF (4.9 mL) and dichloromethane (20 mL) at 0° C. The reaction mixture was stirred at room temperature overnight. After concentrated, the residue was purified by silica gel flash chromatography (petroleum ether:ethyl acetate, 10:1) to give product 8 (4.3 g, 66%). LC-MS: 361.3 $[M+H^+]^+$.

Step 7

Synthesis of (3R,4S)-tert-butyl4-cyclopentyl-3-methoxy-4-(methylamino)butanoate (9)

(3R,4S)-tert-butyl4-(benzyl(methyl)amino)-4-cyclopentyl-3-methoxybutanoate (8) (3.0 g, 8.3 mmol) in ethanol (30 mL) was hydrogenated with Pd/C (1.3 g) for overnight. After the removal of residual Pd/C by filtration, the filtrate was concentrated to afford the desired product 9 (760 mg, 33.6.0%). LC-MS: m/z 272.1$[M+H^+]^+$.

Step 8

Synthesis of (3R,4S)-tert-butyl-4-((S)-2-(benzyloxycarbonylamino)-N,3-dimethylbutanamido)-4-cyclopentyl-3-methoxybutanoate (11)

(3R,4S)-tert-butyl-4-cyclopentyl-3-methoxy-4-(methylamino)butanoate (9). (760 mg, 2.8 mmol) in dichloromethane (10 mL) was added N-Cbz-Val-OH (10) (703 mg, 2.6 mmol), DIPEA (6954) and PyBrop (1.57 g). The reaction mixture was stirred at room temperature overnight. After concentrated, the residue was purified by flash chromatography on silica (petroleum ether:ethyl acetate, 1:10) to give product 11 (420 mg, 30%). LC-MS: m/z 505.0 $[M+H^+]^+$.

Steps 9 and 10

Synthesis of (3R,4S)-tert-butyl-4-((S)-2-amino-N,3-dimethylbutanamido)-4-cyclopentyl-3-methoxybutanoate (12) and (3R,4S)-tert-butyl-4-cyclopentyl-4-((S)—N,3-dimethyl-2-((S)-3-methyl-2-Fmoc-(methylamino)butanamido)butanamido)-3-methoxybutanoate (13)

Compound 11 (400 mg, 0.79 mmol) in ethanol (10 mL) was hydrogenated with Pd/C (50 mg) for 2 hours. After the removal of Pd/C by filtration, the filtrate was evaporated to give desired product 12 (160 mg, 45.5%). LC-MS: m/z 371.0 $[M+H^+]^+$.

Compound 12 (800.0 mg) was dissolved directly in dichloromethane (80 mL), and then 13 (880 mg, 1.2 eq) was added followed by DIEA (0.73 g, 2.5 eq) and HATU (1.02). The reaction mixture was stirred at room temperature for overnight. After concentrated, the residue was purified by silica-gel flash chromatography (petroleum ether:ethyl acetate, 5:1) to give product 14 (1.46 g, 47%). LC-MS: m/z 678.0.0 $[M+H^+]^+$.

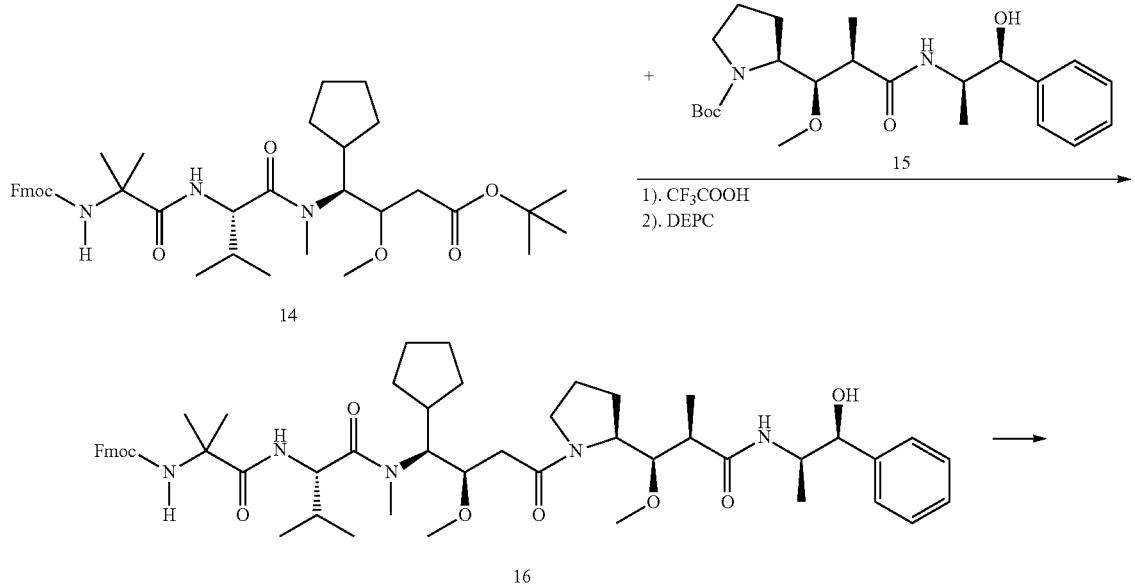

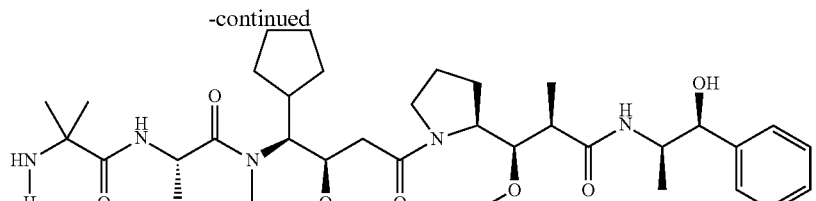

17

Step 11

Synthesis of (9H-fluoren-9-yl)methyl-(S)-2-(2-amino-2-methylpropanamido)-N-((1S,2R)-1-cyclopentyl-4-((S)-2-((1R,2R)-3-((1S,2R)-1-hydroxy-1-phenylpropan-2-ylamino)-1-methoxy-2-methyl-3-oxopropyl)pyrrolidin-1-yl)-2-methoxy-4-oxobutyl)-N,3-dimethylbutanamide (16)

To above product (14) (200.0 mg, 0.3 mmol) and Boc-DAP-OH (15) (127.5 mg, 0.3 mmol) in dichloromethane (7.5 mL) was added trifluoroacetic acid (7.5 mL). The reaction was stirred at room temperature overnight. After concentrated, the residue was dissolved in dichloromethane and evaporated again. This procedure was repeated for 5 times to remove all the residual TFA. The residue dissolved in dichloromethane (15 mL) was neutralized with triethylamine to pH=8 followed by adding more TEA (92 L) and DEPC (53 L). The reaction mixture was stirred at room temperature overnight. After concentrated in vacuo, the desired product 16 was afforded. LC-MS: m/z 925.0 [M+H$^+$]$^+$.

Step 12

(S)-2-(2-amino-2-methylpropanamido)-N-((1S,2R)-1-cyclopentyl-4-((S)-2-((1R,2R)-3-((1S,2R)-1-hydroxy-1-phenylpropan-2-ylamino)-1-methoxy-2-methyl-3-oxopropyl)-pyrrolidin-1-yl)-2-methoxy-4-oxobutyl)-N,3-dimethylbutanamide (17)

To above product (16) was added DEA (3 mL)/CH$_2$Cl$_2$ (3 mL). The reaction mixture was stirred at room temperature overnight. The reaction mixture was washed with water and dried over sodium sulphate. After concentrated in vacuo, the residue was purified by flash chromatography on silica-gel (MeOH/CH$_2$Cl$_2$, 1:10) to give the desired product 17 (121.0 mg, 58.4% for two steps). LC-MS: m/z 703.0[M+H]$^+$; $^1$H NMR (400 MHz, DMSO) δ 8.41 (m, 2H), 7.30-7.11 (m, 5H), 4.80-4.10 (m, 4H), 4.00-3.50 (m, 3H), 3.35-2.65 (m, 14H), 2.44-1.90 (m, 4H), 1.89-1.60 (m, 5H), 1.60 (m, 20H), 1.15-0.70 (m, 6H).

Compound 18 was prepared using the same procedures as 17. Compound 18: 100.0 mg, 48% for final two steps; LC-MS: m/z 717.0 [M+H]$^+$ General Procedures for the Preparation of Products 21 and 22.

Step 1: The tripeptide-O-t-Butyl (0.05 mmol) was treated with TFA (2 mL) in CH$_2$Cl$_2$ (2 mL) for 1 hours at room temperature. The mixture was concentrated to dryness, the residue was co-evaporated with toluene (3×20 mL), and dried in vacuum overnight. The residue was diluted with dichloromethane (5 mL) and added into the deprotected dipeptide Dap-Phe-O-t-butyl (0.50 mmol), followed by DIEA (4 eq.), DEPC (1.1 eq.). After 2 hours at room temperature, the reaction mixture was diluted with ethyl acetate (30 mL), washed with 10% aq citric acid, saturated aq NaHCO$_3$, sat brine. The organic layer was dried and concentrated to give a residue, which was used directly for next step. 20: LC-MS: m/z 995.0 [M+H$^+$].

Step 2: The cleavage of Fmoc was followed the previous procedure as 17 To above product was added DEA (2 mL)/CH$_2$Cl$_2$ (2 mL). The reaction mixture was stirred at room temperature overnight. After washed with H$_2$O, the organic layer was dried and concentrated; the residue was purified by flash chromatography (MeOH/CH$_2$Cl$_2$, 1:10) to give the desired products 21 or 22, respectively. In some cases, the products were further purified by preparative HPLC (Methods C or D).

21: 97.0 mg, 42.6% for three steps; LC-MS: m/z 773.0 [M+H$^+$]. $^1$H NMR (400 MHz, DMSO) δ 8.50-8.30 (m, 2H), 7.31-7.11 (m, 5H), 4.74-4.15 (m, 4H), 3.97-3.69 (m, 2H), 3.55 (m, 1H), 3.31-3.14 (m, 7H), 3.14-2.73 (m, 7H), 2.44-1.91 (m, 6H), 1.70 (m, 5H), 1.58-1.33 (m, 21H), 1.30-0.99 (m, 6H), 0.98-0.80 (m, 6H).

22: (110.0 mg, 48.4% for three steps); LC-MS: m/z 787.0 [M+H$^+$].

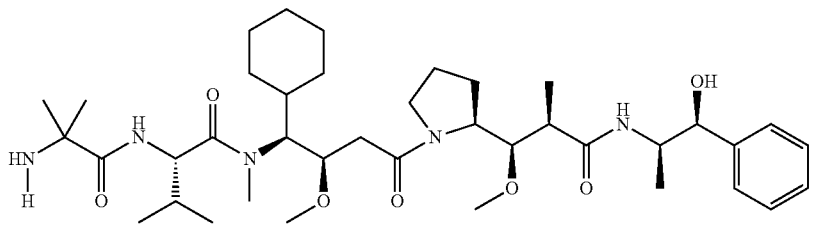

18

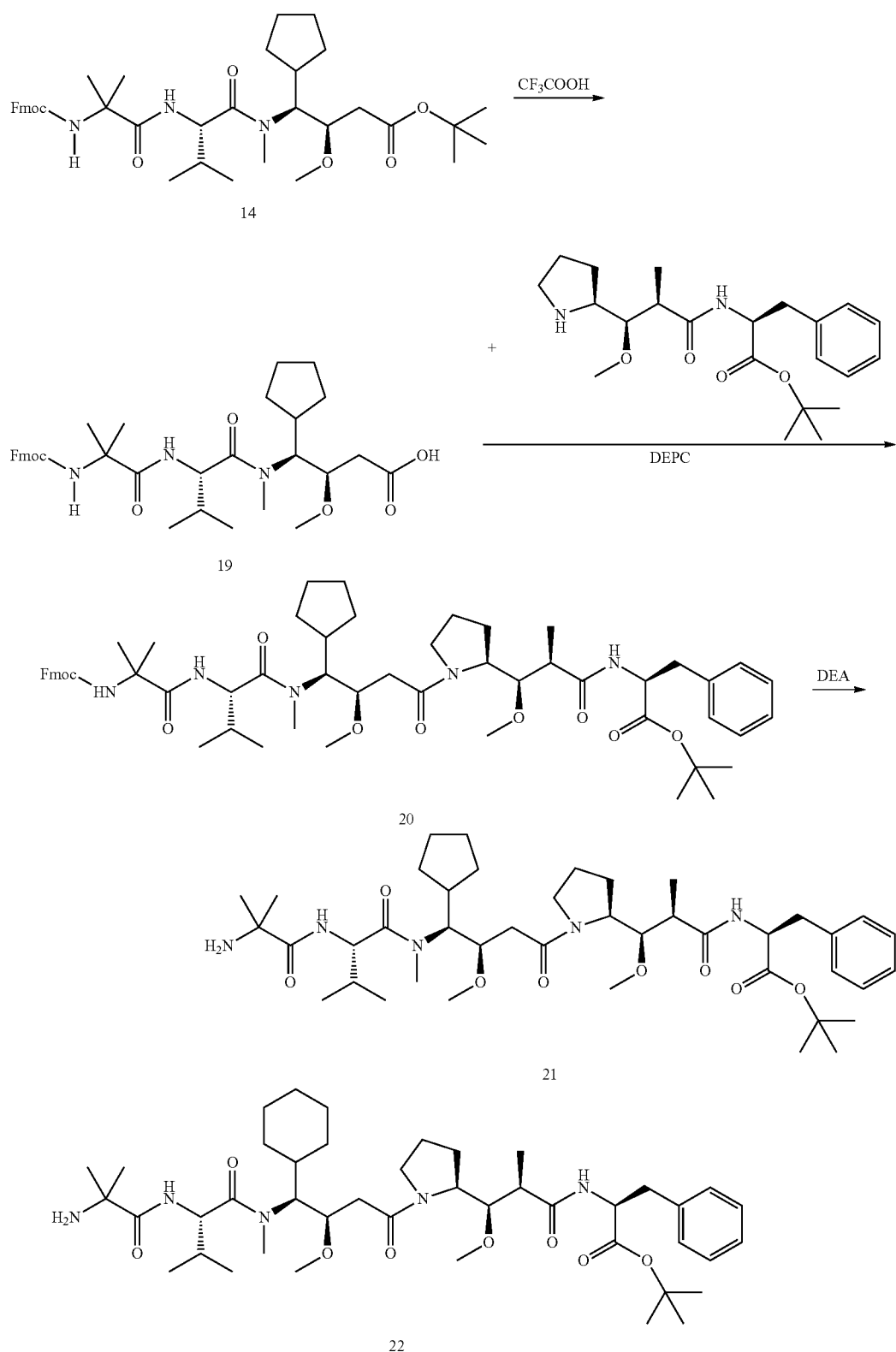
General Procedures for Preparation of Novel Pentapeptide Derivatives 23 and 24 of Dolastatin 10.
The compounds 23 and 24 were prepared by the same procedures as compound 17 (also see US20130129753) as shown in Scheme. The preparation of dolaphine precursor 25 followed literature procedures (*Tetrahedron*, 63, 6155-6123 (2007); US20130129753).

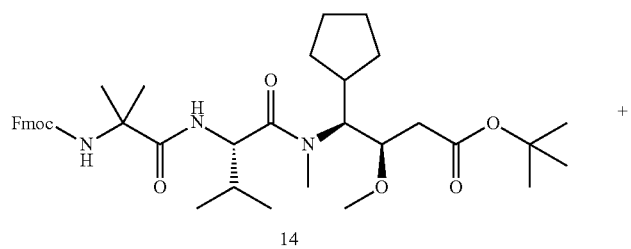
14
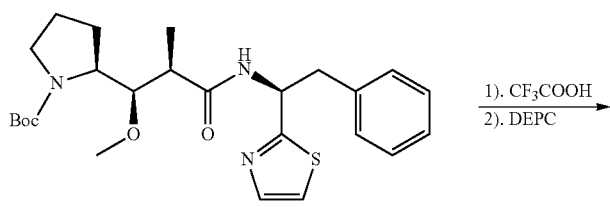
25
1). CF₃COOH
2). DEPC
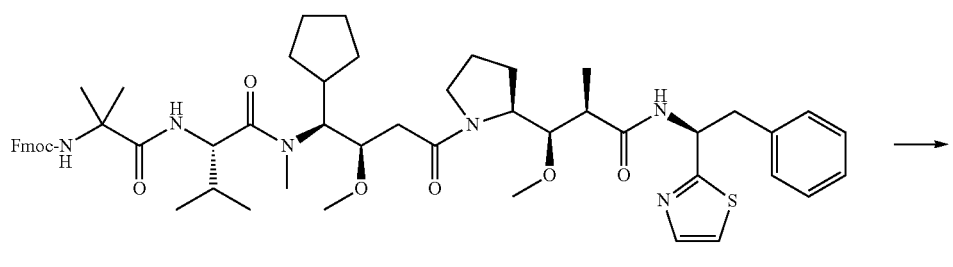
26
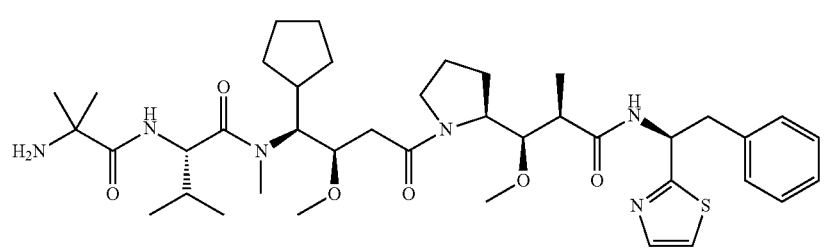
23
Product 23: 111.0 mg, 63.8% for two steps; LC-MS: m/z 756.0[M+H]$^+$; $^1$H NMR (400 MHz, DMSO) δ presumable a mixture of rotamers, [8.93 (d, J=8.6 Hz), 8.67 (d, J=8.4 Hz), 8.52-8.31 (m), 2H], 7.85 (dd, J=10.5, 3.0 Hz, 1H), 7.65 (dd, J=10.8, 3.1 Hz, 1H), 7.37-7.10 (m, 5H), 5.57-5.28 (m, 2H), [4.71 (d, J=5.5 Hz), 4.63 (t, J=8.7 Hz), 1H], 4.53 (t, J=9.1 Hz, 1H), 4.32 (dd, J=18.5, 14.0 Hz, 1H), 3.95-3.75 (m, 2H), 3.61-3.28 (m, 4H), 3.28-3.15 (m, 6H), 3.13-2.58 (m, 6H), 2.44-1.89 (m, 7H), 1.88-1.57 (m, 5H), 1.57-1.35 (m, 10H), 1.35-1.15 (m, 12H), 1.08 (m, 4H), 0.98-0.71 (m, 6H).
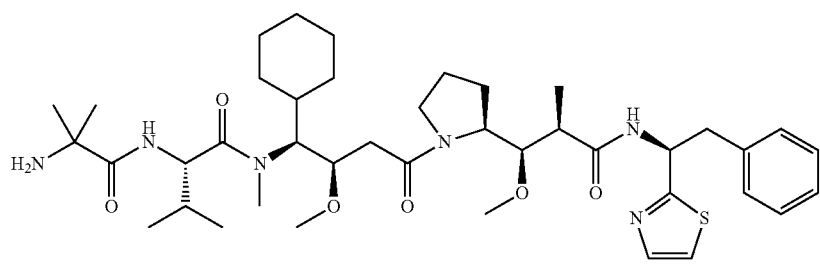
24

Product 24: 142.0 mg, 63.9% for two steps; LC-MS: m/z 770.0[M+H]$^+$; $^1$H NMR (400 MHz, DMSO) δ presumable a mixture of rotamers, [8.98 (d, J=8.0 Hz), 8.67 (d, J=8.0 Hz), 8.52-8.31 (m), 2H, 7.85 (dd, J=16.0 Hz, 4.0 Hz, 1H), 7.65 (dd, J=16.0, 4.0 Hz, 1H), 7.37-7.10 (m, 5H), 5.50-5.25 (m, 2H), 4.80-4.20 (m, 3H), 3.65-3.35 (m, 3H), 3.35-3.15 (m, 7H), 3.10-2.60 (m, 6H), 2.40-1.89 (m, 5H), 1.90-1.50 (m, 8H), 1.55-1.35 (m, 8H), 1.35-1.15 (m, 8H), 1.08-0.71 (m, 6H).

General Procedure for the Linkage of Drugs with the Linkers.

Conjugation of a drug molecule with vc (Val-Cit-PABC), mc (maleimidocaproyl) or PEG linker followed known procedures in WO2004010957 and US 20050238649A1. The yields of linkage of varieties of drugs with cleavable linker vc and non-cleavable linker mc were shown in Table 1.

Preparation of 4-((S)-2-((S)-2-(6-(2,5-dioxo-2,5-dihydro-1H-pyrrol-1-yl)hexanamido)-3-methylbutanamido)-5-ureidopentanamido)benzyl-1-((S)-1-(((1S,2R)-1-cyclopentyl-2-methoxy-4-((S)-2-((1R,2R)-1-methoxy-2-methyl-3-oxo-3-((S)-2-phenyl-1-(thiazol-2-yl)ethylamino)propyl)pyrrolidin-1-yl)-4-oxobutyl)(methyl)amino)-3-methyl-1-oxobutan-2-ylamino)-2-methyl-1-oxopropan-2-ylcarbamate (27)

To a solution of mcValCitPABC (1.0 eq) and drug 23 (1.0 eq) in DMF was added Hunig's base (4 eq), 2,6-lutidine (4 eq) and HOAT (0.2 eq). The reaction mixture is allowed to stir for 30 minutes at room temperature. Reaction is monitored by LC-MS. After the completion, the reaction is concentrated and purified by flash chromatography, then by C$_{18}$ medium pressure reversed phase chromatography (gradient: 5% acetonitrile to 100% acetonitrile containing 0.1% TFA).

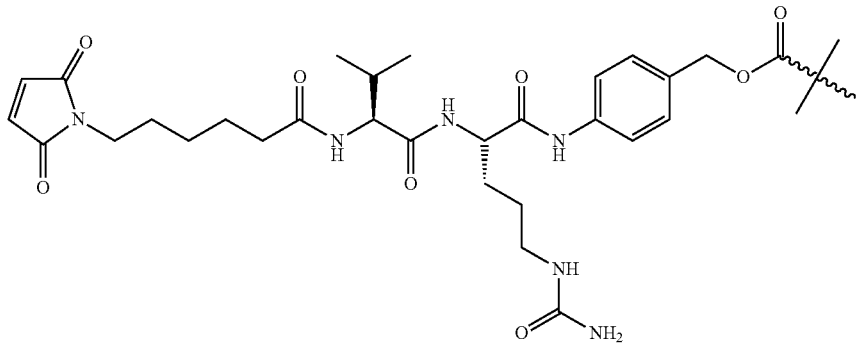

Vc (Val-Cit-PABC) Linker Unit

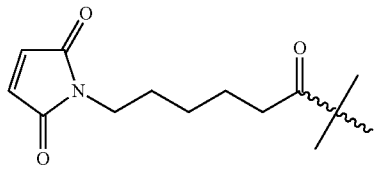

MC (Maleimidocaproyl) Linker Unit

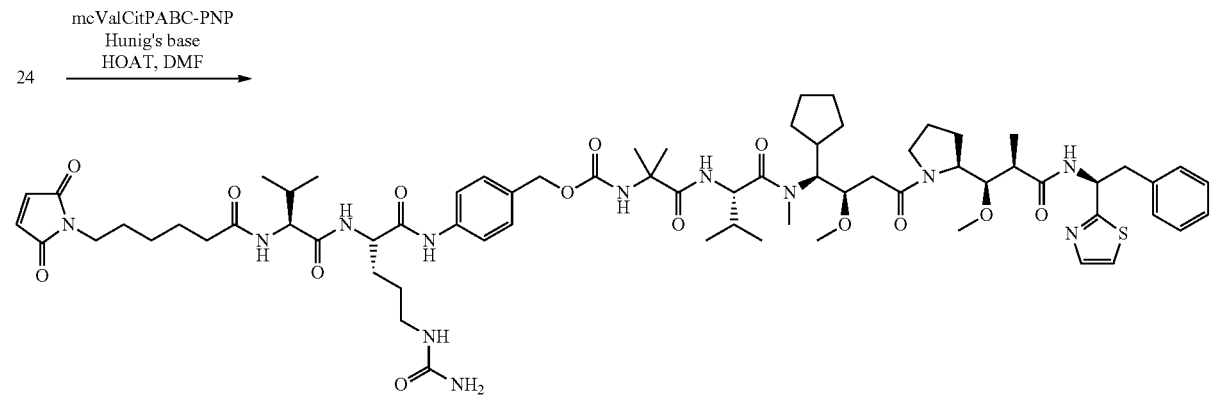

27: 20.0 mg, 36.1%; LC-MS: m/z 1354.0 [M+H$^+$]. $^1$H NMR (400 MHz, DMSO) δ presumable a mixture of rotamers: 9.98 (s, 1H), [8.88 (d, J=8.5 Hz), 8.66 (d, J 8.2 Hz), total 1H], 8.09 (d, J=8.0 Hz, 1H), 7.50-7.80 (m, 5H), 7.10-7.50 (m, 10H), 7.00 (s, 2H), 5.97 (brs, 1H), 5.35 (m, 3H), 4.94 (s, 2H), 4.30-4.80 (m, 3H), 4.19 (m, 1H), 3.81 (m, 2H), 3.46 (m, 5H?), 3.20 (m, 7H), 3.00 (m, 7H), 1.88-2.44 (m, 10H), 0.95-1.80 (m, 39H).

The compounds 28, 29 and 30 were prepared using the same procedure as 27 and the yields were shown in Table 1.

Preparation of (S)-tert-butyl-2-((2R,3R)-3-((S)-1-((3R,4S)-4-cyclopentyl-4-((S)-2-(2-(6-(2,5-dioxo-2,5-dihydro-1H-pyrrol-1-yl)hexanamido)-2-methylpropanamido)-N,3-dimethylbutanamido)-3-methoxybutanoyl)pyrrolidin-2-yl)-3-methoxy-2-methylpropanamido)-3-phenylpropanoate (31)

A stirring solution 7-(2,5-dioxo-2,5-dihydro-1H-pyrrol-1-yl) heptanoic acid (1.2 eq), HATU (1.2 eq), and Hunig's base (3 eq) in DMF and dichloromethane is allowed to stir for 30 minutes. Compound 21 (1 eq) is then added as a solution in dichloromethane and DMF. Reaction is monitored by LC-MS. The reaction is concentrated and purified by flash chromatography, then by C$_{18}$ medium pressure reversed phase chromatography (gradient: 5% acetonitrile to 100% acetonitrile containing 0.1% TFA).

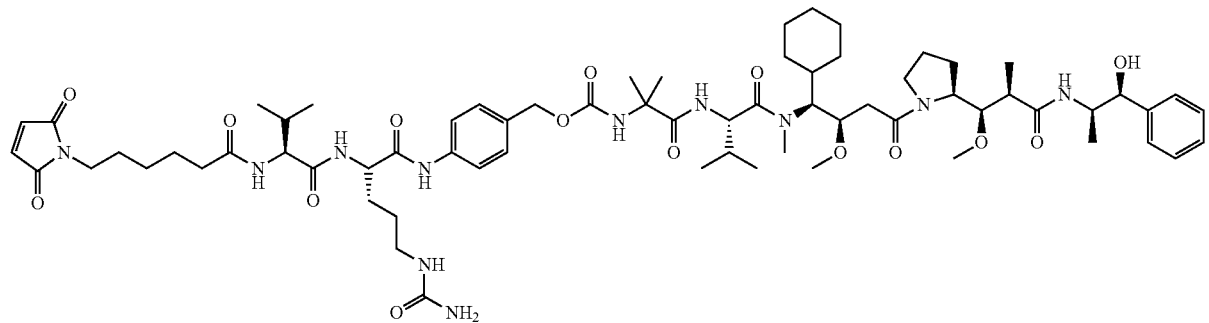

28

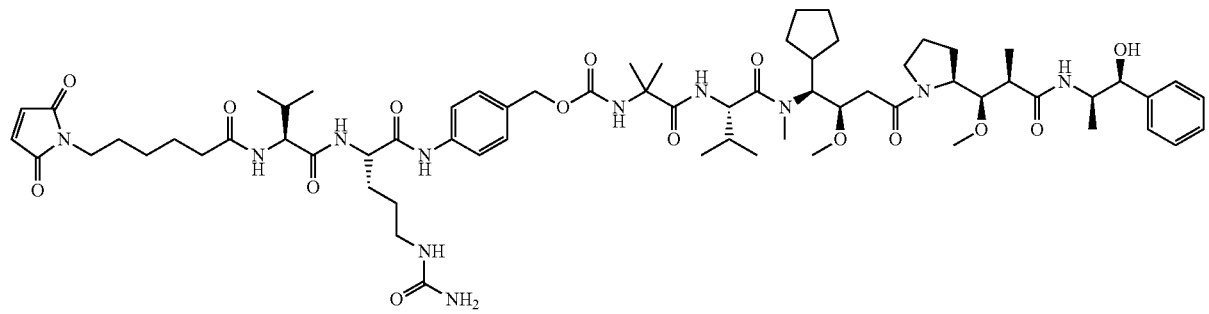

29

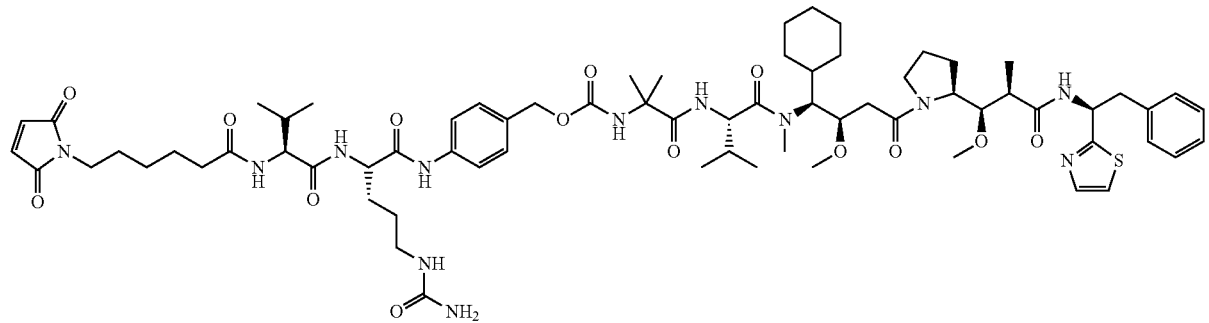

30

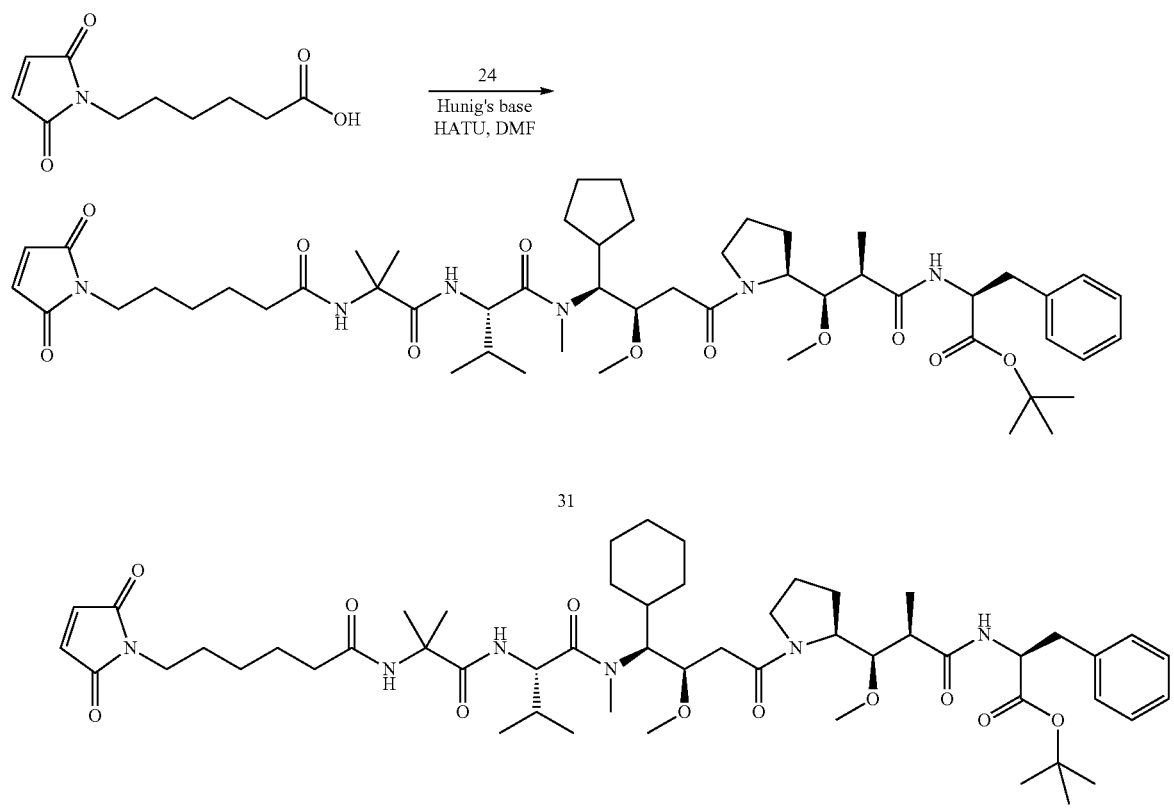

TABLE 1

Linkage of drugs with cleavable or non-cleavable linkers

| payloads-linkers # | payloads# | Payloads (mg) | payload-linkers yield[a] mg (%) |
|---|---|---|---|
| 27 | 24 | 34 | 20 (36.1) |
| 28 | 18 | 20 | 9.5 (25.7) |
| 29 | 17 | 35 | 28 (43.8) |
| 30 | 23 | 30 | 18 (32.8) |
| 31 | 21 | 40 | 14 (28.0) |
| 32 | 22 | 20 | 8.3 (33.8) |

[a]The yields (%) of payload-linker were isolated yield and determined by the mol ratio of payload-linker and payload.

Results and Discussion

A family of novel cytotoxins derived from dolastatins or auristatins were designed and synthesized. The present disclosed pentapeptides showed very potent antitumor activities against cancel cell lines Hela, A549, HCC1954 and SK-BR-3 as shown in Table 2.

TABLE 2

$IC_{50}$ for selected compounds (cytotoxic peptide) of the present invention

| Cytotoxins# | Hela (nM) | A549 (nM) | HCC1954 (nM) | SK-BR-3 (nM) | MCF-7 (nM) |
|---|---|---|---|---|---|
| 01 (17) | 1.560 | 6.317 | 0.623 | 0.839 | 4.753 |
| 02 (18) | 0.478 | 1.143 | 0.466 | 0.805 | 3.186 |
| 03 (23) | 0.484 | 2.830 | 0.405 | 0.693 | 2.901 |
| 04 (24) | 0.571 | 3.344 | 0.310 | 0.524 | 1.990 |
| 05 (21) | 0.563 | 1.134 | 0.296 | 0.223 | 1.300 |
| 06 (22) | 0.567 | 1.083 | 0.112 | 0.066 | 0.529 |
| Cisplatin | 181.504 | 2834.490 | 3265.863 | 853.526 | 3551.395 |

6 days exposure.

In Table 3, the ADCs prepared from Herceptin (Trastuzumab) showed extreme potency against Her2 positive breast cancer cell lines HCC1954 and SK-BR-3. The $IC_{50}$ values were low as 0.1 polemol for H-vc17. The most importantly, H-vc18 ADC was at least 10 fold better than H-vcMMAE for potency, selectivity and efficiency as shown in FIG. 1A to FIG. 1C and FIG. 2A to FIG. 2C. However, the conjugates were highly inactive against MCF7, which does not overexpress Her2 ($IC_{50}$>50 nM). In addition, the conjugate from IgG1 control was highly inactive against Her2 positive breast cancer cell lines HCC1954 and SK-BR-3.

TABLE 3

$IC_{50}$ measured for payloads17 to 24 and related ADCs (6 days exposure)

| | HCC1954 | SK-BR-3 | MCF-7 | DAR |
|---|---|---|---|---|
| 17 | 0.623 | 0.839 | 4.753 | — |
| IgG1-vc17 | 0.504 | 0.747 | 3.503 | 3.8 |
| H-vc-17 | 0.003 | 0.0001 | 2.541 | 3.6 |
| 18 | 0.466 | 0.805 | 3.186 | — |
| IgG1-vc18 | 19.034 | 28.724 | >50 | 3.8 |
| H-vc-18 | 0.006 | <0.001 | 24.552 | 3.6 |
| 21 | 0.296 | 0.223 | 1.300 | — |
| IgG1-mc21 | 48.713 | 51.152 | 60.604 | 4.1 |
| H-mc21 | 0.116 | 0.012 | >50 | 2.1 |
| 22 | 0.112 | 0.066 | 0.529 | — |
| IgG1-mc22 | 20.304 | 20.360 | 70.442 | 4.1 |
| H-mc22 | 0.122 | 0.012 | 39.551 | 3.7 |
| 23 | 0.405 | 0.693 | 2.901 | — |
| IgG1-vc23 | 4.606 | 7.469 | 34.162 | 3.1 |
| H-vc-23 | 0.079 | 0.022 | 6.970 | 2.8 |
| 24 | 0.310 | 0.524 | 1.990 | |
| IgG1-vc24 | 1.224 | 1.534 | 3.606 | 2.5 |
| H-vc-24 | 0.961 | 1.048 | 4.177 | 3.8 |
| MMAE | 0.073 | 0.103 | 0.321 | — |

TABLE 3-continued

IC$_{50}$ measured for payloads 17 to 24 and related ADCs (6 days exposure)

| | HCC1954 | SK-BR-3 | MCF-7 | DAR |
|---|---|---|---|---|
| IgG1-vcMMAE | 33.590 | 41.463 | >50 | 2.9 |
| H-vcMMAE | 0.094 | 0.017 | 43.686 | 3.1 |

H: Herceptin,
vc: linker;
DAR: drug-antibody ratio

The present invention disclosed a family of novel cytotoxic pentapeptides, which showed potent antitumor activities against several cancer cells, including Hela, A549, MCF-7, HCC-1954 and SK-BR-3, but not limited to those cancer cell lines. A series of Herceptin ADCs prepared from these novel payloads showed high potency against Her2 positive breast cancer cell lines. At least one of these ADCs showed much better potency, selectivity and efficiency compared with Herceptin-vcMMAE. Novel payloads/ADC platform may be very useful for improving therapeutic index (TI) of ADCs in clinical trials and applications, as well as for discovery and development of novel ADC candidates.

We claim:

1. Compounds having the following structures:

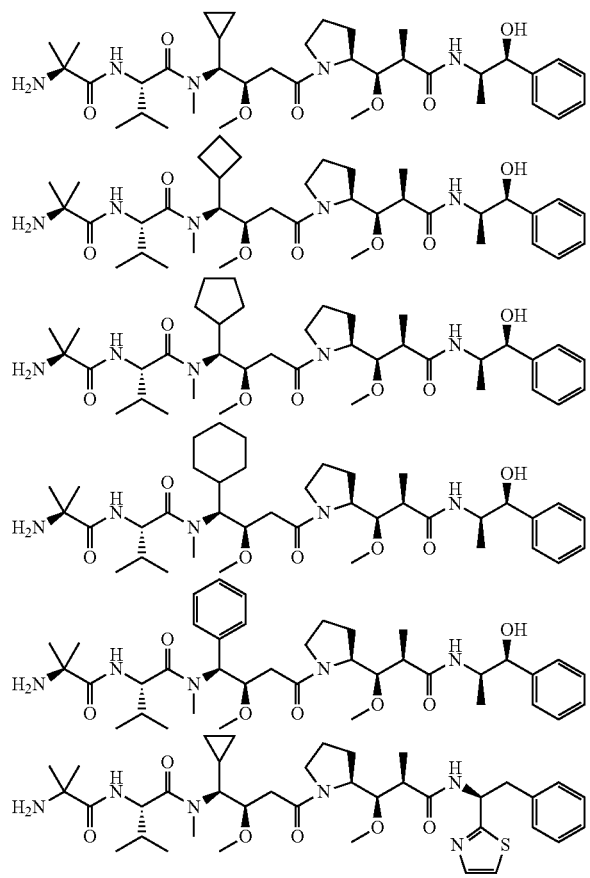
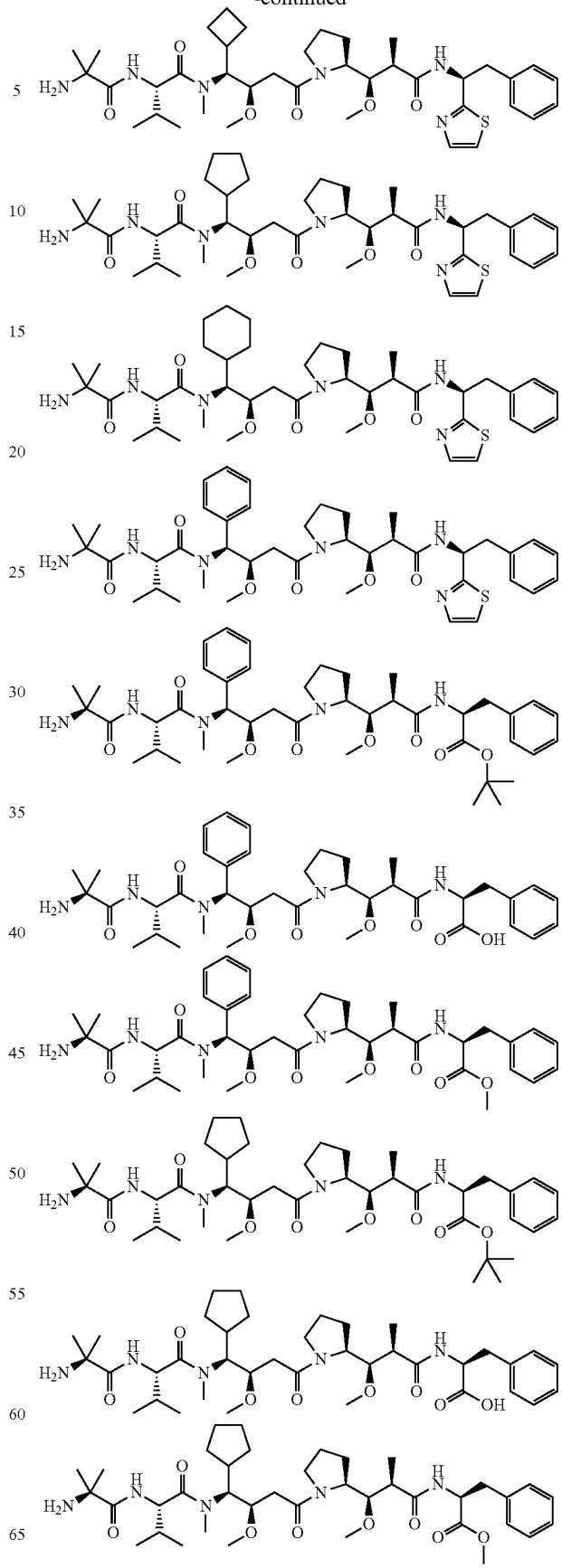

57
-continued
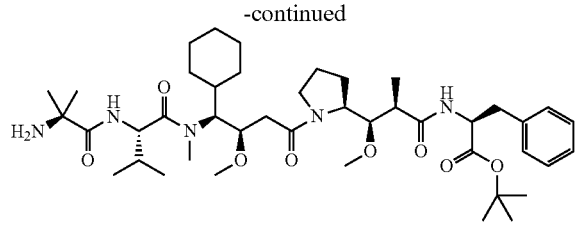
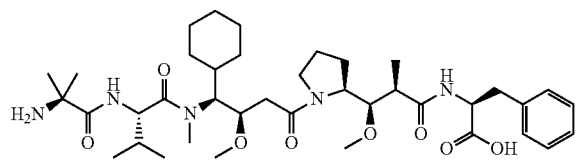
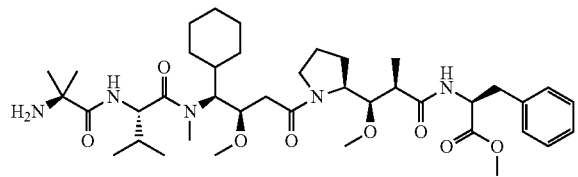
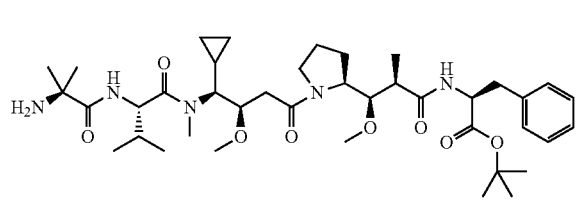
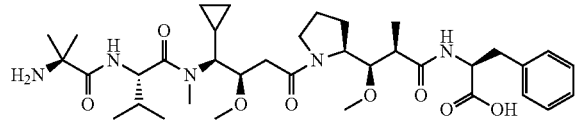
58
-continued
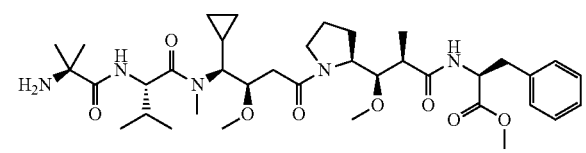
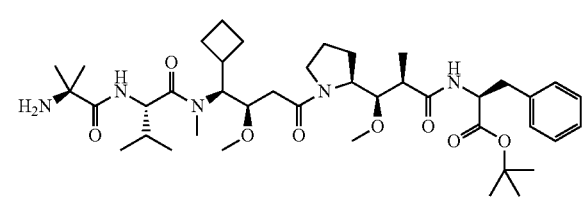
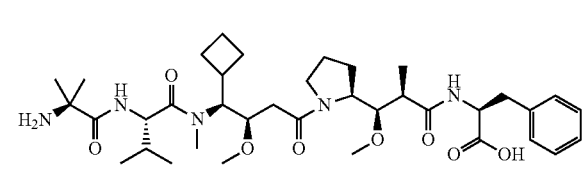
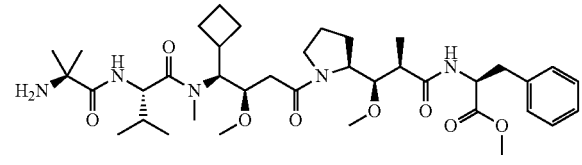
2. Drug-linker compounds having the following structures:
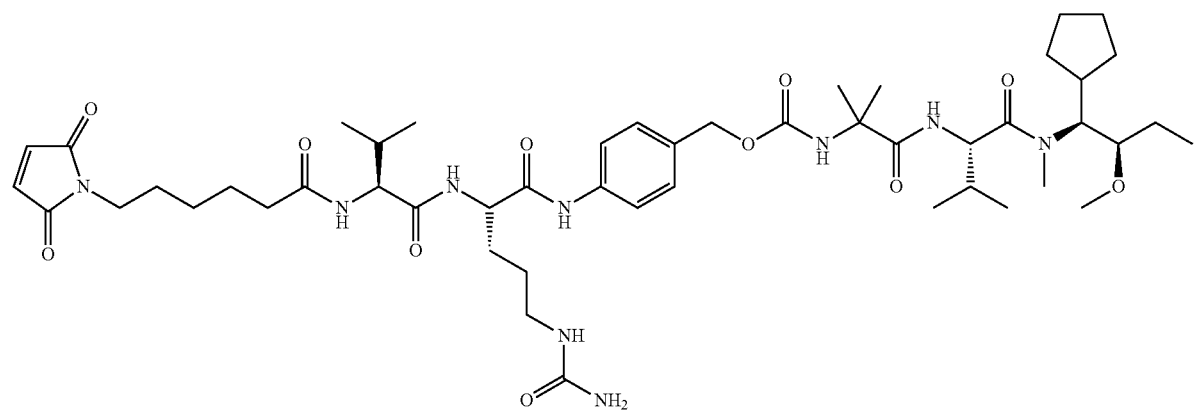
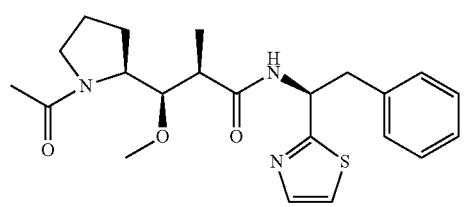

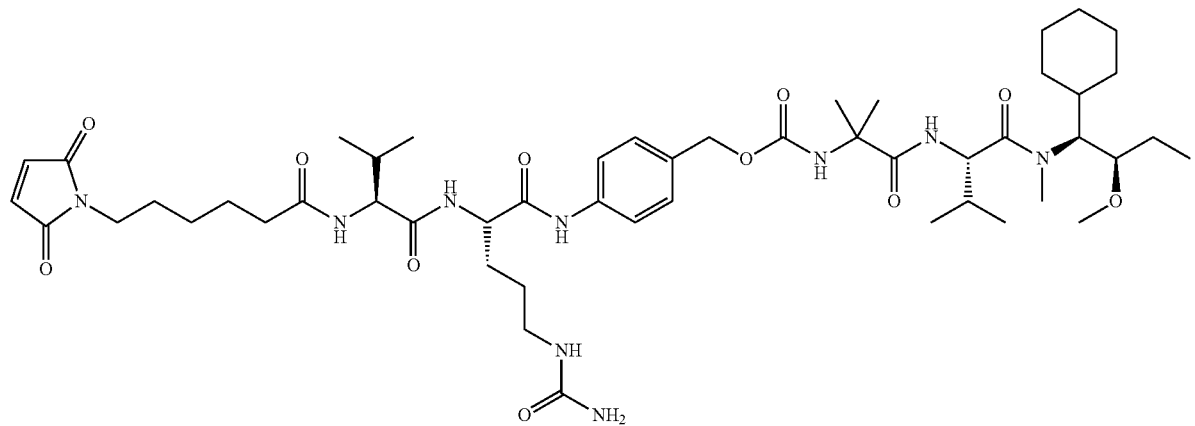
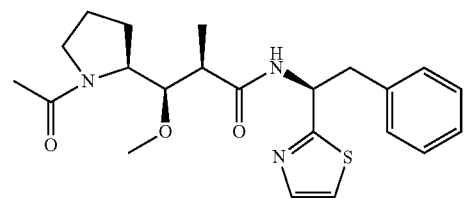
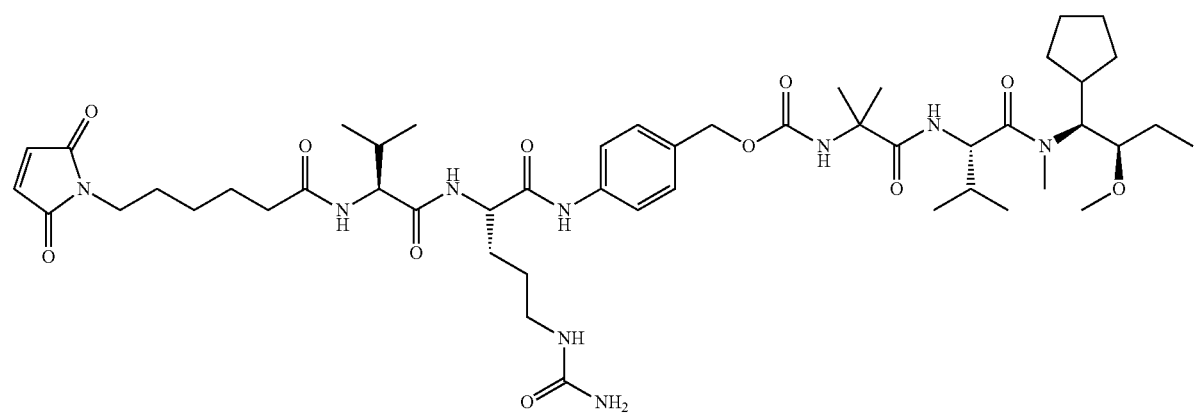
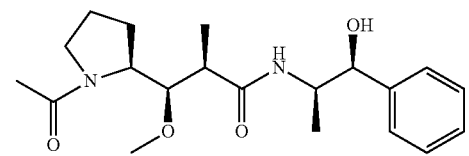
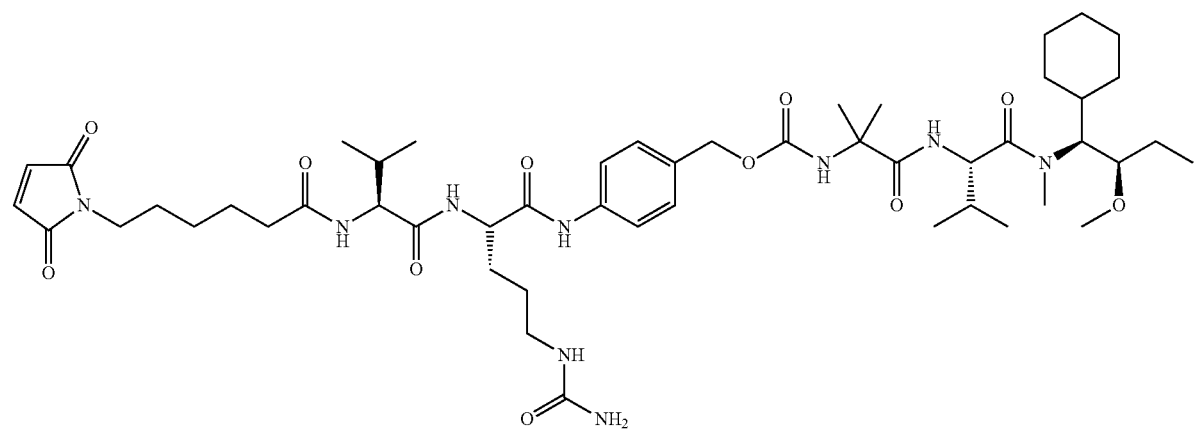

-continued
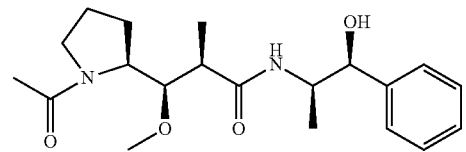
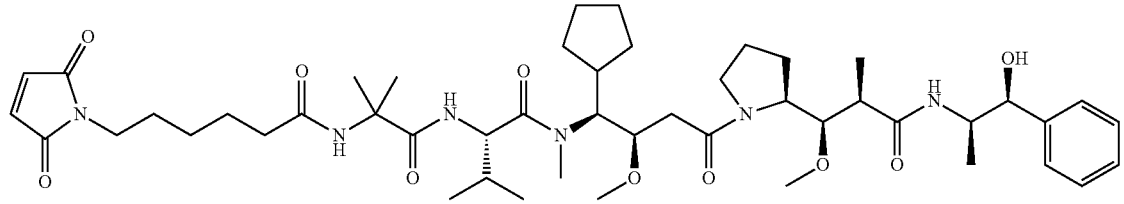
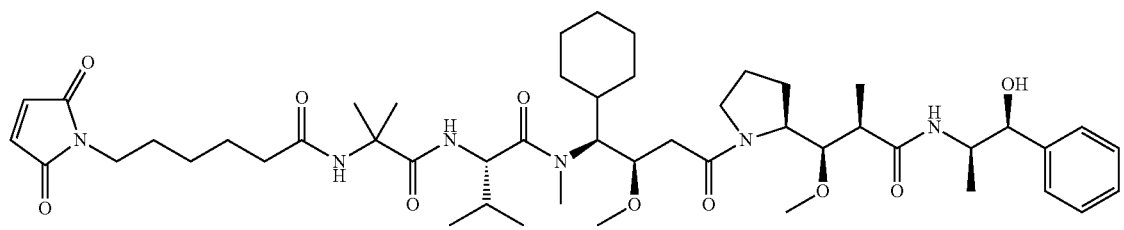
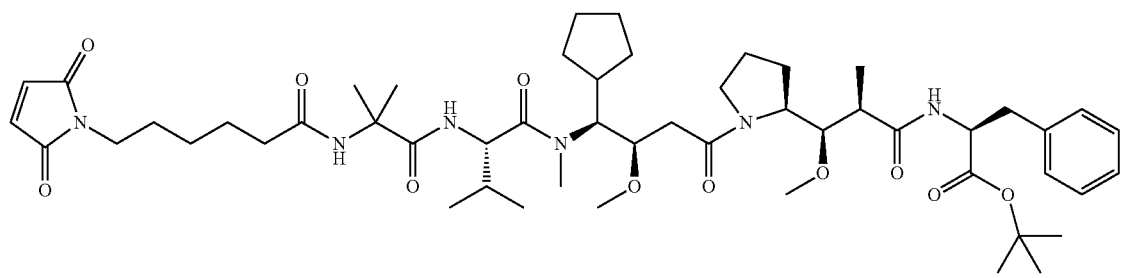
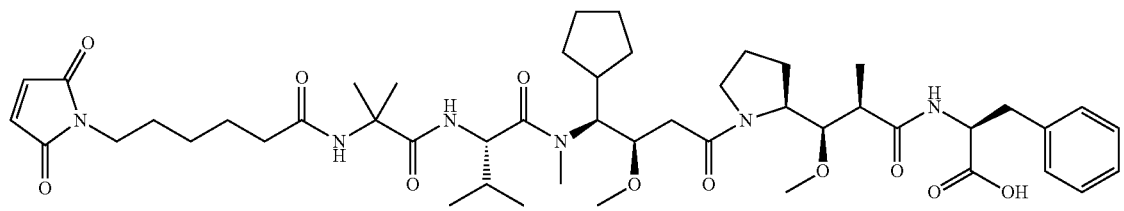
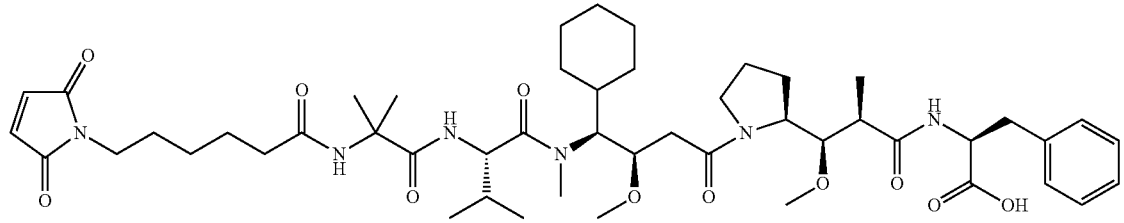
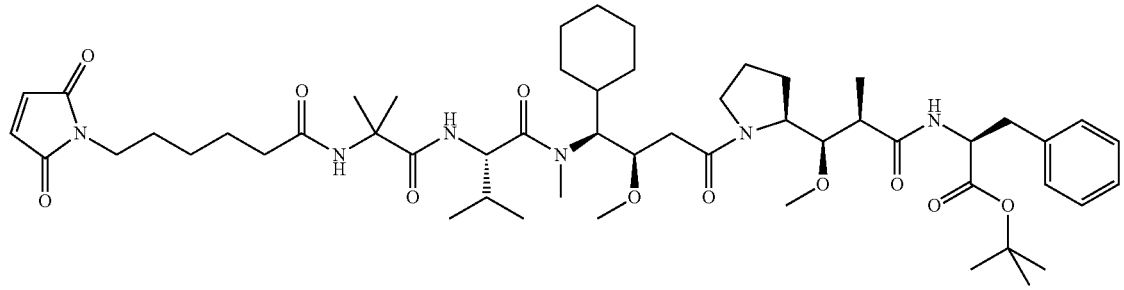

-continued
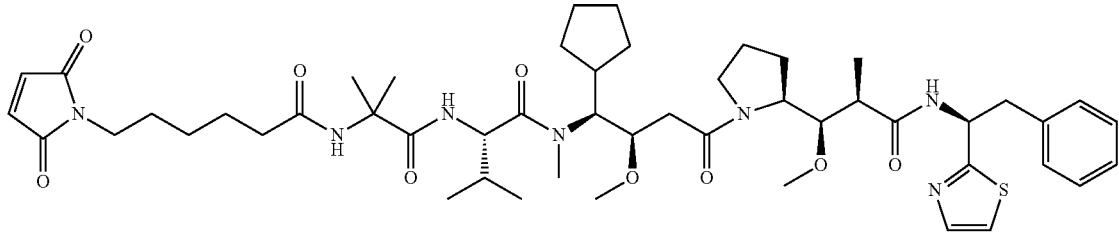
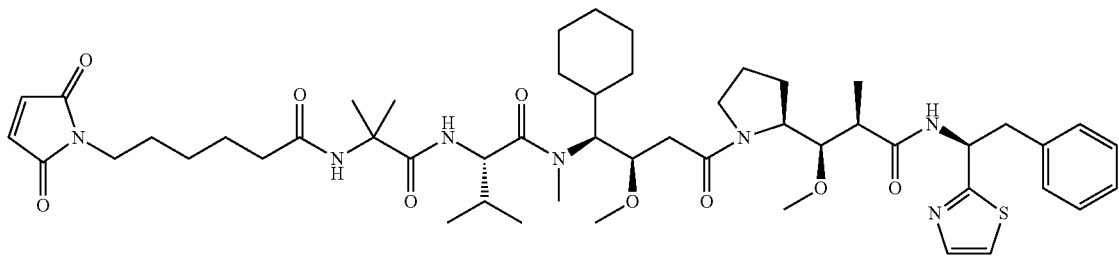
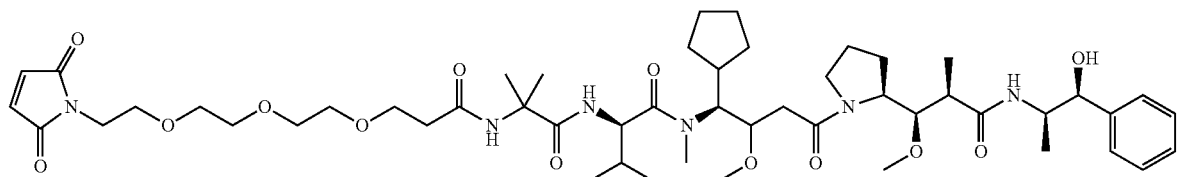
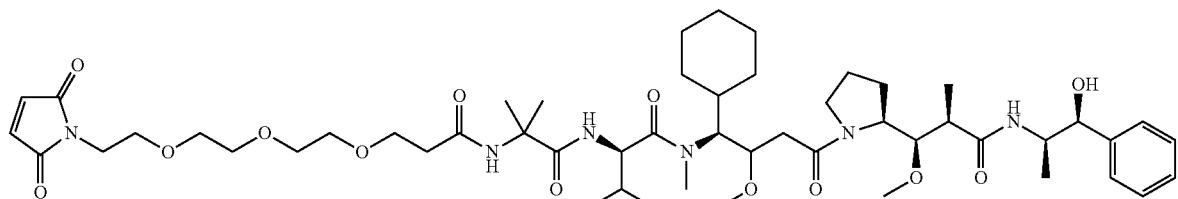
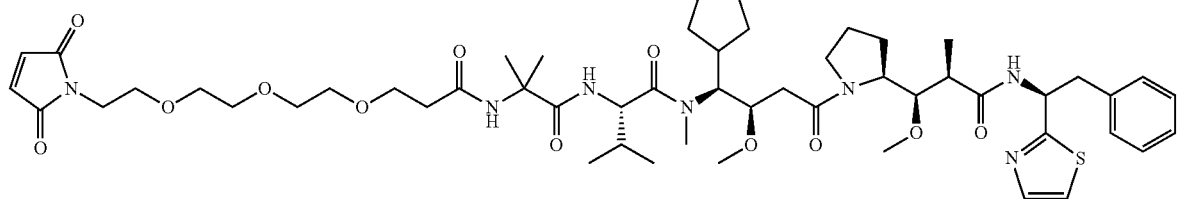
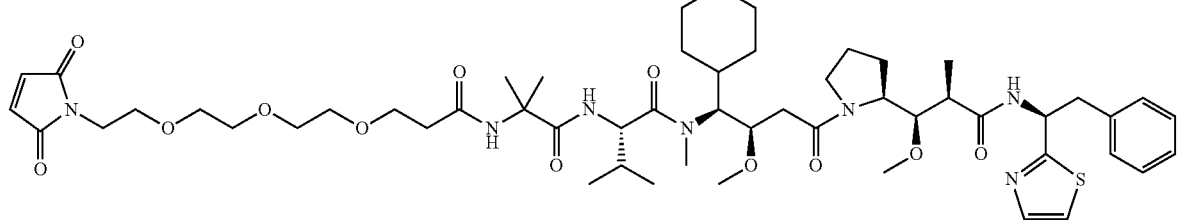
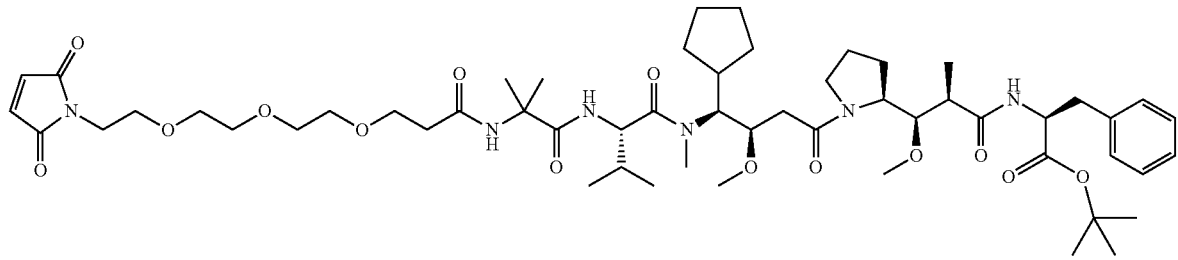

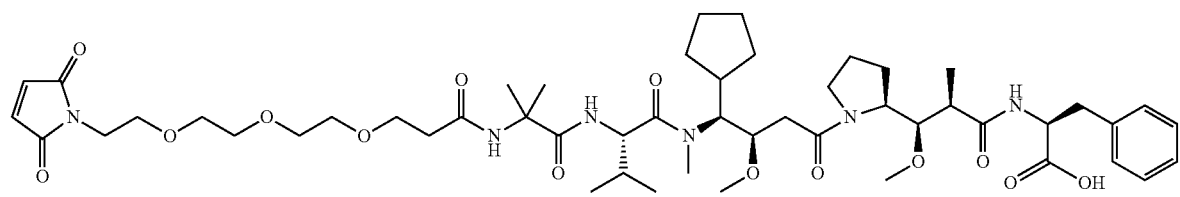
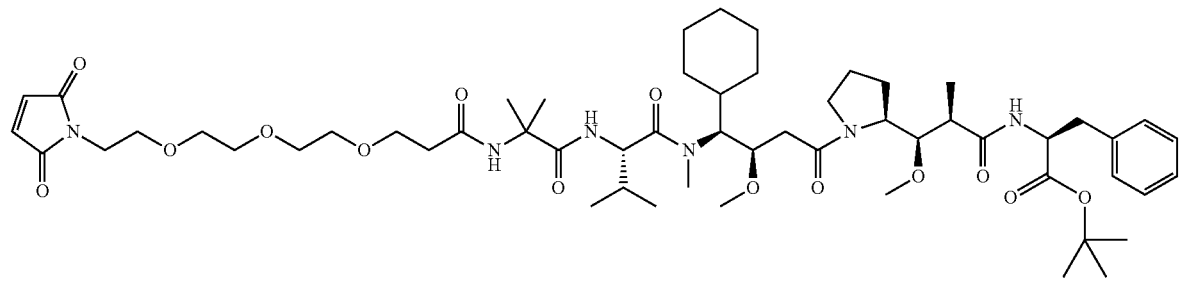
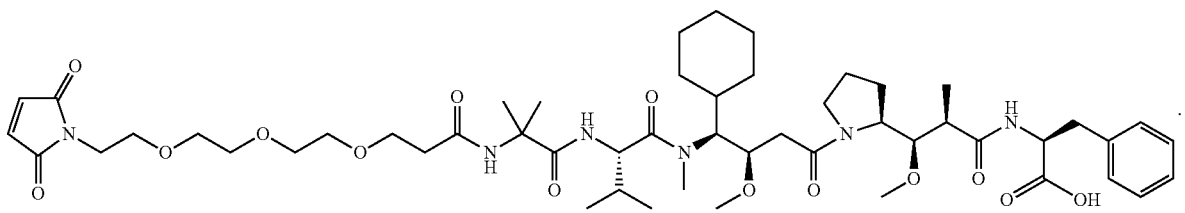
3. A drug conjugate or pharmaceutically acceptable salt of a drug conjugate having the formula:
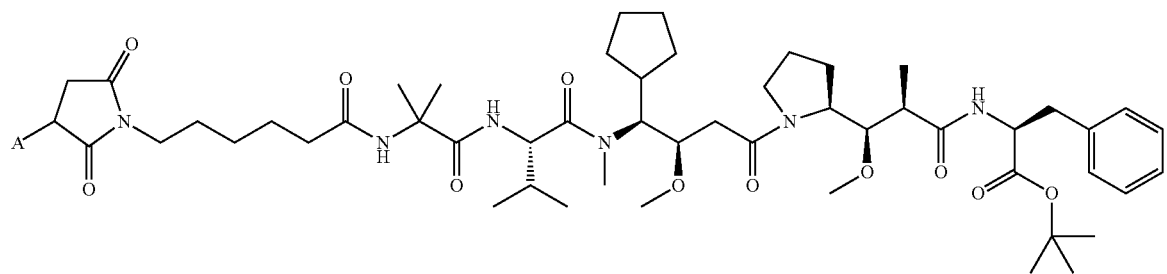
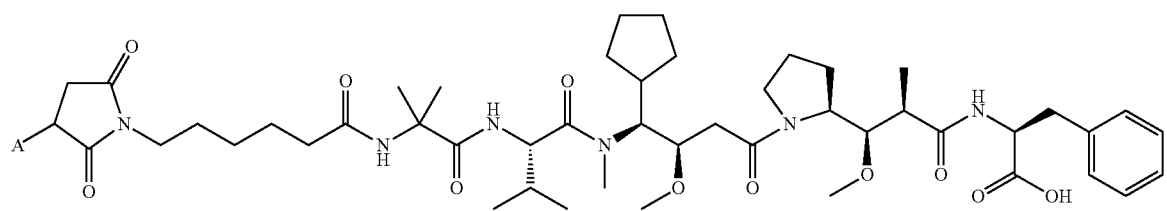
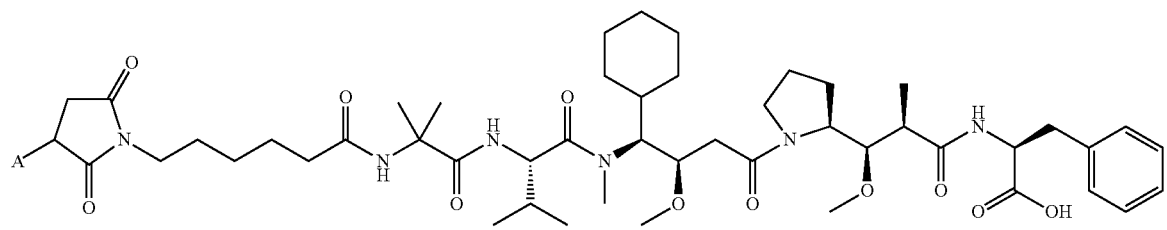

-continued
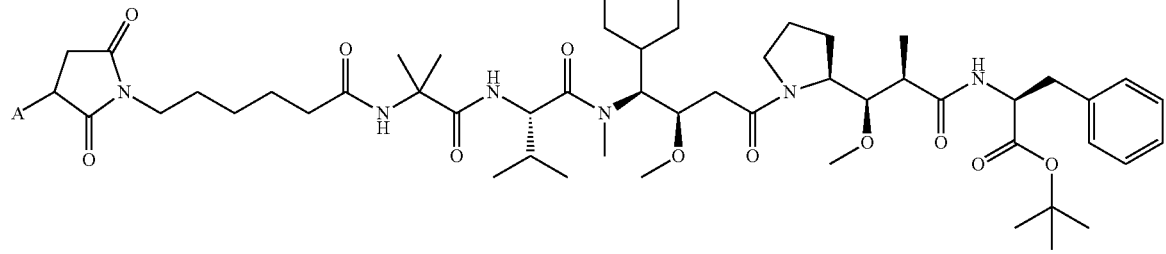
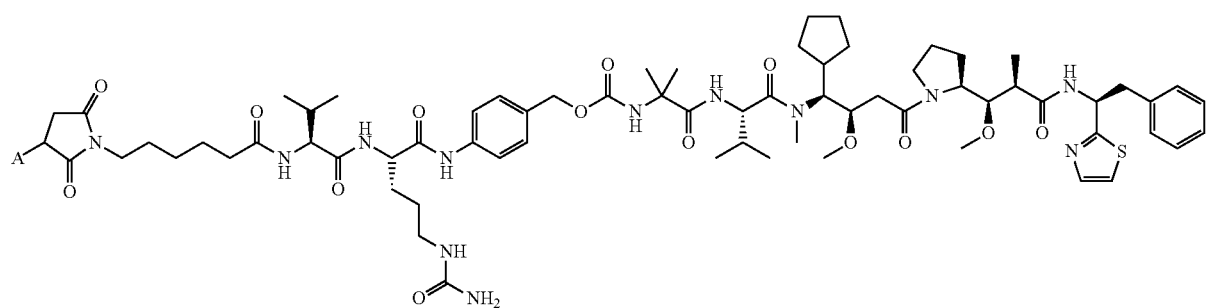
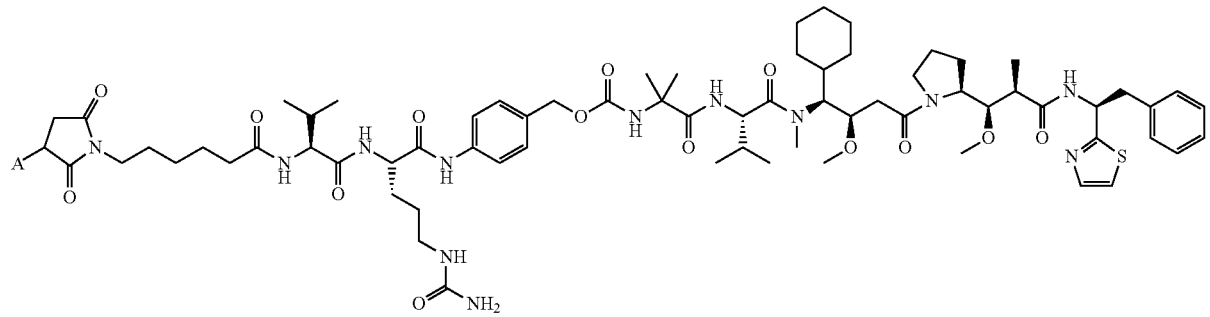
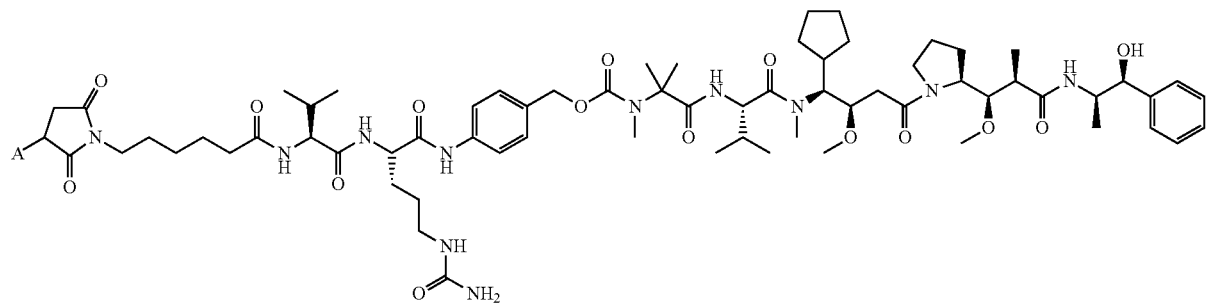
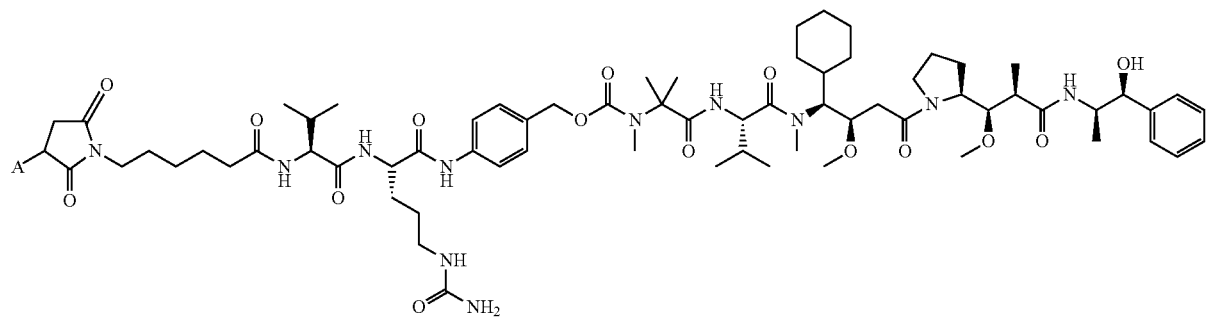

-continued
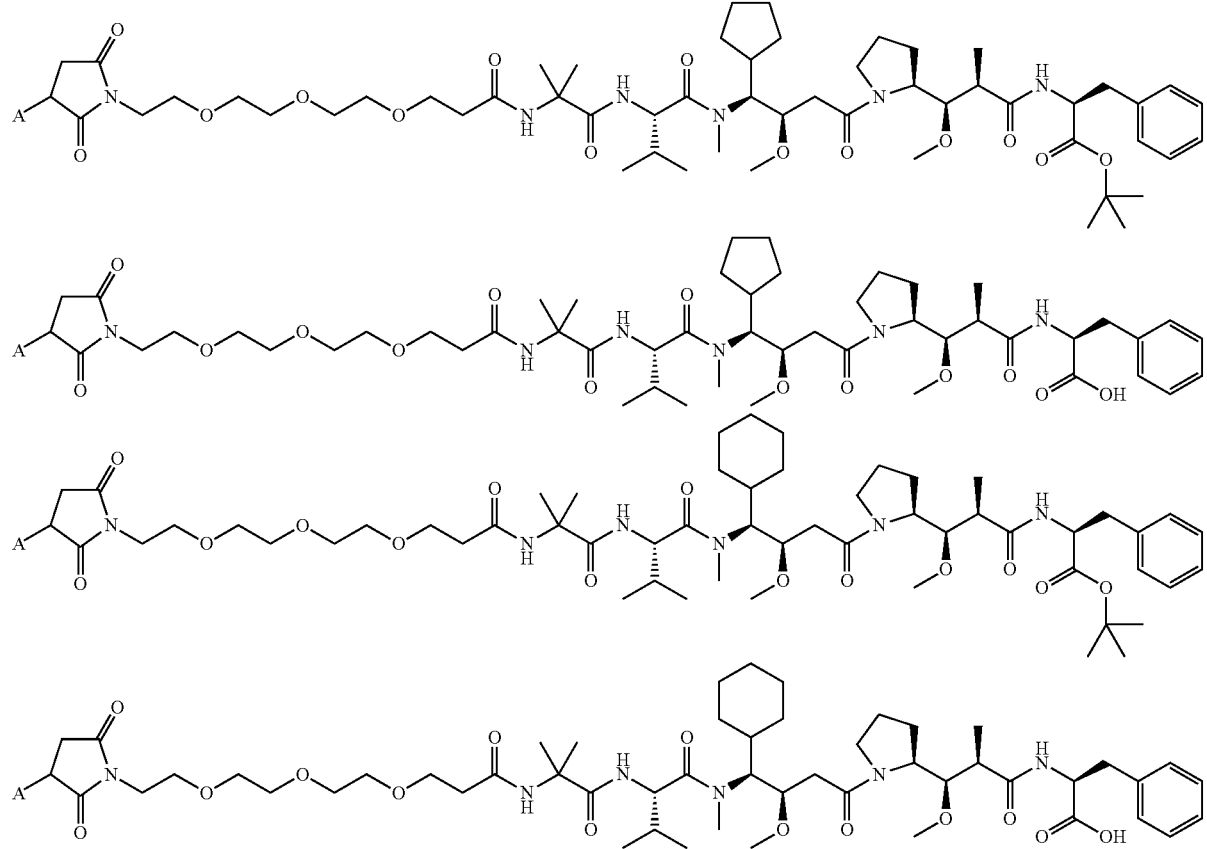
where A is an antibody.
* * * * *